(12) United States Patent
Roush

(10) Patent No.: US 10,866,114 B2
(45) Date of Patent: Dec. 15, 2020

(54) ANALOG WELLNESS DEVICE

(71) Applicant: Garmin Switzerland GmbH

(72) Inventor: Adam W. Roush, Prairie Village, KS (US)

(73) Assignee: Garmin Switzerland GmbH

( * ) Notice: Subject to any disclaimer, the term of this patent is extended or adjusted under 35 U.S.C. 154(b) by 37 days.

(21) Appl. No.: 16/015,029

(22) Filed: Jun. 21, 2018

(65) Prior Publication Data

US 2018/0299292 A1 Oct. 18, 2018

Related U.S. Application Data

(63) Continuation of application No. 14/718,991, filed on May 21, 2015, now Pat. No. 10,030,994.

(51) Int. Cl.
*G04G 21/02* (2010.01)
*G04C 3/14* (2006.01)
(Continued)

(52) U.S. Cl.
CPC .......... *G01C 22/006* (2013.01); *A61B 5/1118* (2013.01); *A61B 5/681* (2013.01); *G04C 3/146* (2013.01); *G04G 21/025* (2013.01); *A61B 5/742* (2013.01); *G04B 47/00* (2013.01); *G04B 47/063* (2013.01); *G04G 9/0064* (2013.01); *G04G 21/04* (2013.01); *G08B 5/226* (2013.01); *G08B 5/228* (2013.01)

(58) Field of Classification Search
None
See application file for complete search history.

(56) References Cited

U.S. PATENT DOCUMENTS 7,072,246 B2 * 7/2006 Lizzi .................... G04B 19/082
116/292
7,859,951 B2 * 12/2010 Plancon .................. G04C 9/00
368/80

(Continued)

FOREIGN PATENT DOCUMENTS

| JP | 2013215346 | 10/2013 |
| JP | 2015047208 | 3/2015 |
| KR | 100319948 | 1/2002 |

OTHER PUBLICATIONS

Printout from http://www.cookoo2.com/, published prior to May 21, 2015.

(Continued)

*Primary Examiner* — John C Kuan
(74) *Attorney, Agent, or Firm* — Samuel M. Korte; Max M. Ali

(57) ABSTRACT

Embodiments are disclosed to monitor and present biometric information for a user wearing a watch. The watch may include a biometrics sensor configured to output biometric signals associated with a user wearing the watch and a processor configured to select one of a plurality of alphanumeric characters based upon the determined biometric information. The watch may include a first disc coupled with a first motor and including the plurality of alphanumeric characters, the first disc positioned under the first window such that one of the plurality of alphanumeric characters, such as a target heart rate zone, is visible through the first window as the first motor rotates the first disc.

17 Claims, 12 Drawing Sheets

(51) Int. Cl.
*A61B 5/00* (2006.01)
*G04B 47/00* (2006.01)
*G04G 9/00* (2006.01)
*G04B 47/06* (2006.01)
*G01C 22/00* (2006.01)
*A61B 5/11* (2006.01)
*G08B 5/22* (2006.01)
*G04G 21/04* (2013.01)

(56) References Cited

U.S. PATENT DOCUMENTS

| | | | |
|---|---|---|---|
| 9,295,413 B2 | 3/2016 | Lee et al. | |
| 9,594,354 B1 | 3/2017 | Kahn | |
| 10,030,994 B2 | 7/2018 | Roush | 702/160 |
| 2004/0233788 A1* | 11/2004 | Plancon | G04B 19/082 368/11 |
| 2006/0073851 A1* | 4/2006 | Colando | G04G 9/0064 455/566 |
| 2013/0286793 A1 | 10/2013 | Umamoto | |
| 2014/0009258 A1 | 1/2014 | Case | 340/5.2 |
| 2014/0200691 A1 | 7/2014 | Lee | |
| 2014/0357317 A1* | 12/2014 | Mullen | H04M 1/72527 455/557 |
| 2015/0061889 A1 | 3/2015 | Kotaki | |
| 2015/0085622 A1 | 3/2015 | Carreel | |
| 2015/0093725 A1 | 4/2015 | Baarman et al. | 434/127 |
| 2016/0174857 A1* | 6/2016 | Eggers | G06F 19/3418 600/301 |
| 2016/0259299 A1 | 9/2016 | Kahn | |
| 2018/0032997 A1* | 2/2018 | Gordon | G06Q 20/3224 |

OTHER PUBLICATIONS

Printout from http://www2.withings.com/us/en/products/activite/, published prior to May 21, 2015.
Printout from http://www.eziosmartwear.com/#functionmeetfashion , published prior to May 21, 2015.
Printout from http://www.avi-8nation.com/collections/shop-all/products/av-4006-02-hawker-harrier-II , published prior to May 21, 2015.
Printout from http://cogitowatch.com/ , published prior to May 21, 2015.
Printout from http://nevowatch.com/?v=7516fd43adaa , published prior to May 21, 2015.
Printout from http://breva-watch.com/en/watch/genie-02-terre/ , published prior to May 21, 2015.
Printout from http://blueangelscitizenwatch.watches-reviews.com/images/casio-watches-2.jpg , published prior to May 21, 2015.
International Search Report and Written Opinion from Corresponding PCT PCT/US2016/031252, filed May 6, 2016.

* cited by examiner

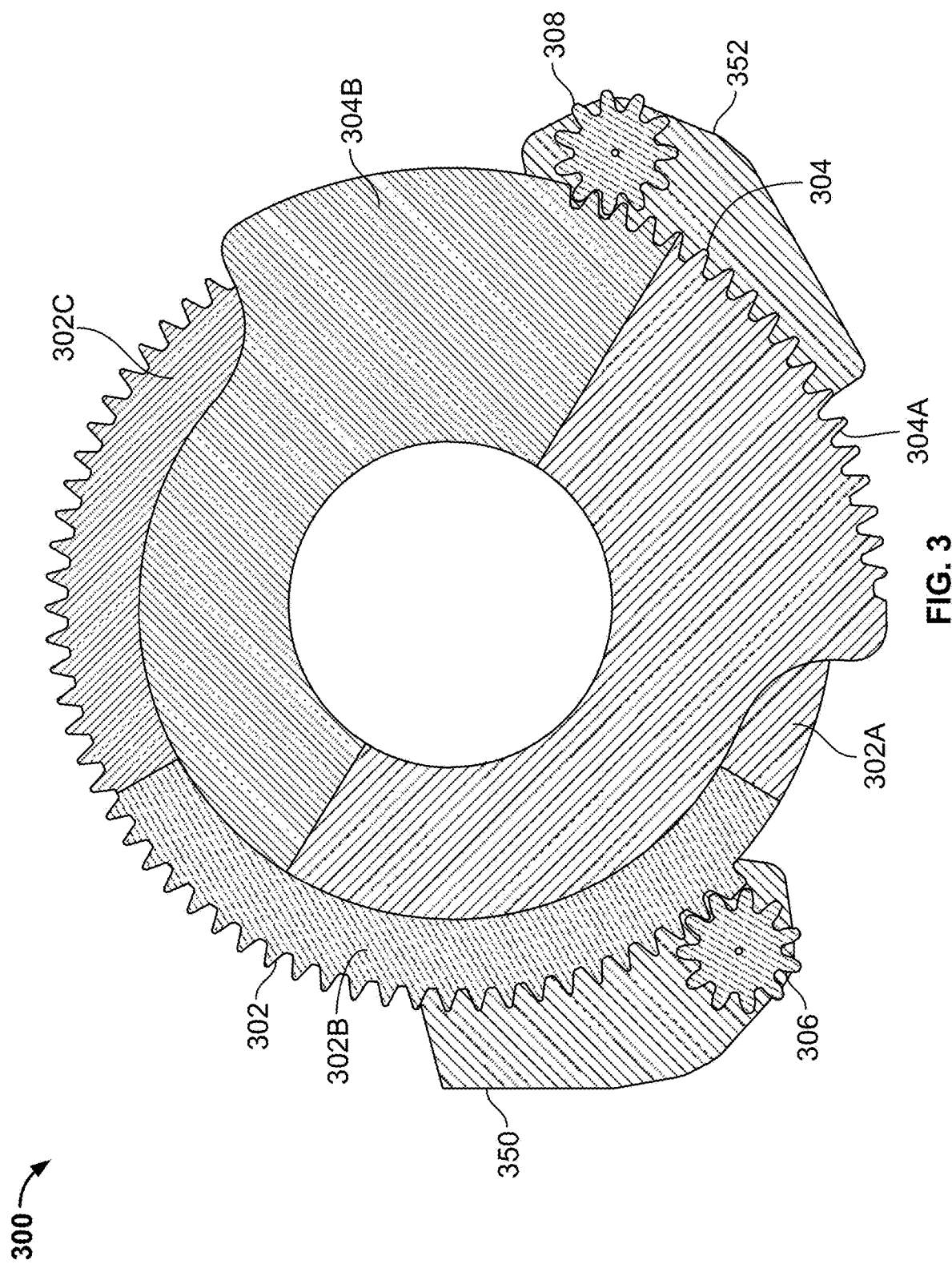

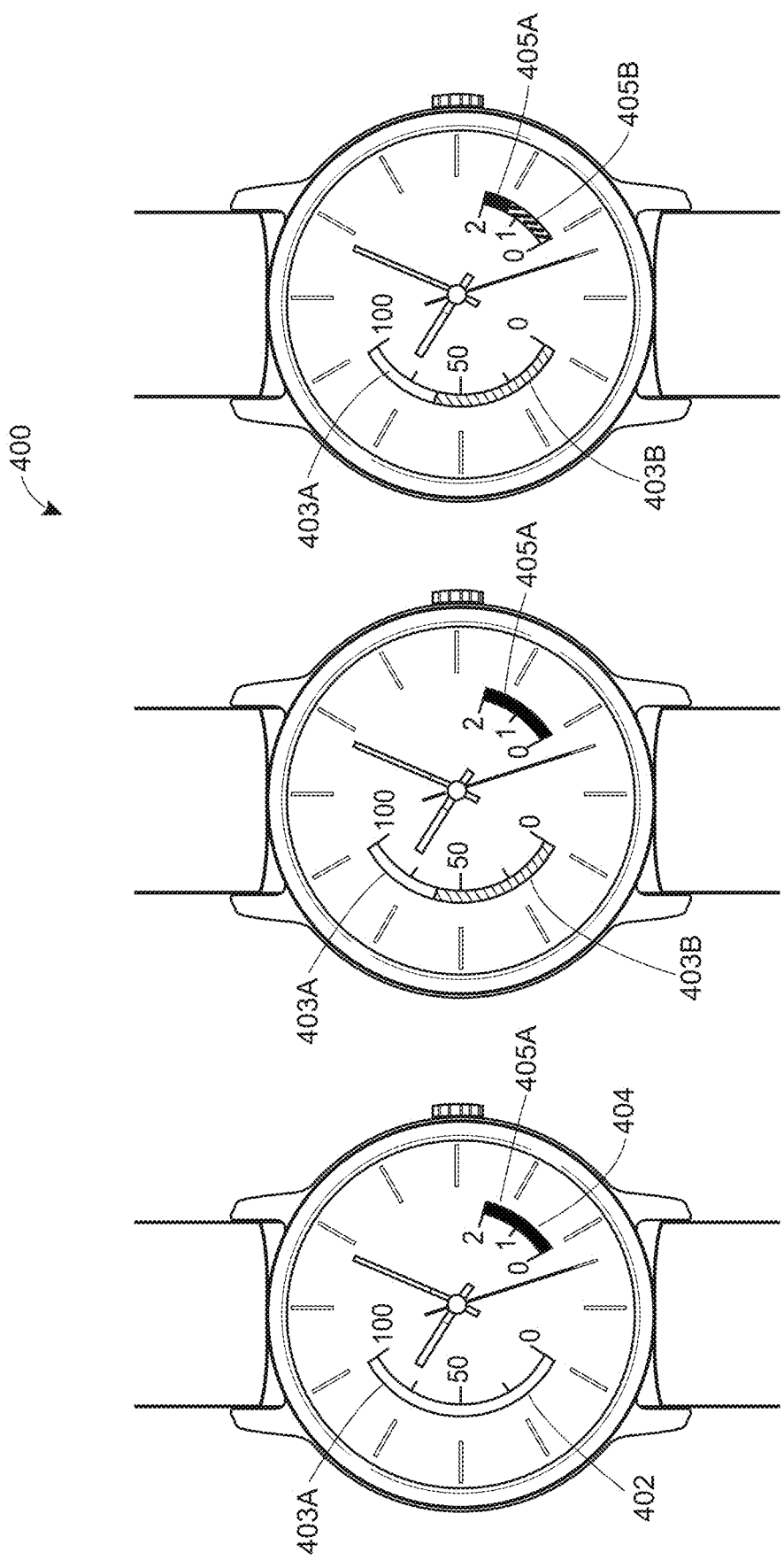

ANALOG WELLNESS DEVICE

RELATED APPLICATION

The present application is a continuation of, and claims priority benefit to, co-pending and commonly assigned U.S. non-provisional patent application entitled "Analog Wellness Device," application Ser. No. 14/718,991, filed May 21, 2015. This earlier-filed application is hereby incorporated by reference into the current application in its entirety

BACKGROUND

Users of wrist worn devices, such as watches, commonly wish to track and view their physical activity over a period of time and receive communications in a simple and intuitive manner. Conventional activity tracking devices may determine a number of steps a user takes throughout the day as part of a fitness activity goal and display this information using a display component so the user can gauge his progress towards meeting the goal. However, conventional activity monitoring devices typically utilize digital display components, which may not be aesthetically pleasing when implemented in some wearable devices such as watches. Digital display components also consume relatively large amounts of power and therefore need to be frequently recharged. Additionally, digital display components typically must be large and bright to be easily visible during various uses and lighting environments. Furthermore, although conventional activity tracking devices may display user activity, these devices do not measure or present user inactivity. As a result, current techniques of tracking and displaying user activity have several drawbacks.

Conventional watches may include one or more secondary watch arms positioned above the watch face and one or more rotating discs positioned behind the watch face to communicate information. A conventional analog watch that includes one or more secondary watch arms, independent of the hour and minute arms used to indicate a current time, may communicate information presented at a perimeter area of each respective secondary watch arms. A conventional analog watch that includes one or more rotating discs positioned behind the watch face may rotate at a predetermined rate to communicate information provided on a top surface of each respective disk when exposed through an opening in the watch face. The secondary watch arms and rotating discs may rotate at a predetermined rate to indicate calendar information (e.g., current month, current day of the week, current day of the month, lunar information, etc.) to a user. Some conventional watches may rotate a secondary watch arm to provide fitness information, such as number of steps taken. Some conventional watches include one or more digital displays positioned behind the watch face such that a portion of each respective display is visible through openings of the watch face.

SUMMARY

Embodiments of the present technology relate generally to an analog wellness device and, more particularly, to an analog watch that provides various types of information, such as a user's activity and inactivity levels, one or more notifications regarding connectivity, communications, and/or operation of one or more external devices in communication with the analog wellness device, a user's biometric information, information related to an activity the user is engaged in, etc.

Embodiments are disclosed describing an analog wellness device to monitor and provide a user's physical activity, which may be implemented as an analog watch. The analog watch may use a position of watch arms commonly known to indicate a time of day and rotating discs to communicate information such as user activity, user inactivity, and/or other types of information to a user.

The analog watch may communicate this information to a user using any suitable combination of full and/or partial discs corresponding to the particular information to be provided. For instance, the analog wellness device may include motors that are coupled to respective discs having distinct regions such that, when rotated to one of a plurality of rotational positions, one or more portions of the distinct regions are visible through one or more windows in the watch face.

For example, the first of these motors may rotate a first multicolored disc based upon a measured number of steps taken by the user, which may be part of a threshold number of steps associated with a daily fitness activity goal to indicate an activity level. As the first motor rotates the first multicolored disc, the colors shown through a first window indicate a proportion of the fitness activity goal that has been met or exceeded. The second of these motors may turn a second multicolored disc based upon a period of time associated with the user's inactivity to indicate an inactivity level. The one or more colors presented through a second window may indicate the period of time that the user has been inactive. The period of time may accumulate as the user is inactive and recede as the measured number of steps increases, thereby providing an immediate incentive to engage in physical activity.

To provide another example, one or more of these motors may rotate a respective disc in a clockwise and/or a counterclockwise rotational direction to provide various information through one or more windows in the watch face. For instance, each respective disc may have various symbols, labels, text, emoticons, symbols, indicia, emoji, graphics, etc., indicative of different types of information such as received communications from a mobile phone (e.g., missed calls, new emails, battery level, etc.), heart rate, and information to assist a golfer while playing a course, etc. Additionally or alternatively, the watch hands may facilitate relaying some of this information to the user.

This summary is provided to introduce a selection of concepts in a simplified form that are further described below in the detailed description. This summary is not intended to identify key features or essential features of the claimed subject matter, nor is it intended to be used to limit the scope of the claimed subject matter. Other aspects and advantages of the present technology will be apparent from the following detailed description of the embodiments and the accompanying drawing figures.

BRIEF DESCRIPTION OF THE DRAWINGS

The figures described below depict various aspects of the system and methods disclosed herein. It should be understood that each figure depicts an embodiment of a particular aspect of the disclosed system and methods, and that each of the figures is intended to accord with a possible embodiment thereof. Further, whenever possible, the following description refers to the reference numerals included in the following figures, in which features depicted in multiple figures are designated with consistent reference numerals.

FIG. 3 is an illustration 300 of two exemplary multicolored discs used to indicate a user's activity and inactivity, according to an embodiment;

FIG. 4A is an illustration of an exemplary analog watch 400 registering no steps being taken by a user and no inactivity time, according to an embodiment;

FIG. 4B is an illustration of an exemplary analog watch 400 indicating a proportion of steps taken by a user towards accomplishing a fitness activity goal and no inactivity time, according to an embodiment;

FIG. 4C is an illustration of an exemplary analog watch 400 indicating a proportion of steps taken by a user towards accomplishing a fitness activity goal and some inactivity time, according to an embodiment;

DETAILED DESCRIPTION

Figure 1:
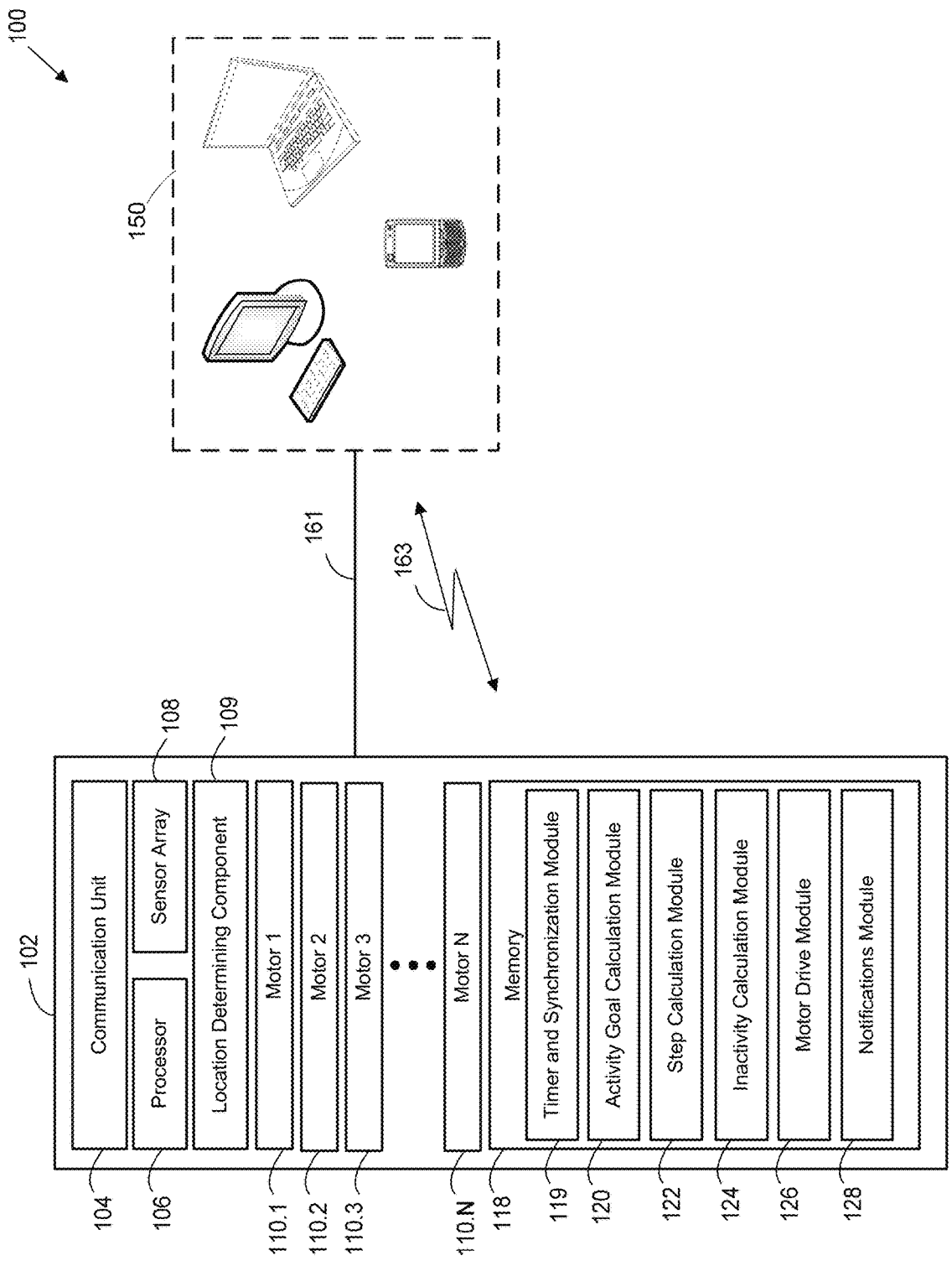
FIG. 1 is an illustration of a block diagram of an exemplary analog wellness system 100 in accordance with an embodiment of the present disclosure.

The following text sets forth a detailed description of numerous different embodiments. However, it should be understood that the detailed description is to be construed as exemplary only and does not describe every possible embodiment since describing every possible embodiment would be impractical. In light of the teachings and disclosures herein, numerous alternative embodiments may be implemented.

It should be understood that, unless a term is expressly defined in this patent application using the sentence "As used herein, the term '_____' is hereby defined to mean . . . " or a similar sentence, there is no intent to limit the meaning of that term, either expressly or by implication, beyond its plain or ordinary meaning, and such term should not be interpreted to be limited in scope based on any statement made in any section of this patent application.

As further discussed in detail below, an analog wellness system is described that may include an analog wellness device and an external computing device, which may communicate with one another. The external computing device may communicate with the analog wellness device to set an initial reference time, to set an initial fitness activity goal in terms of threshold number of steps to be taken by a user over a specific period of time, communicate the receipt of incoming communications (e.g., a number of missed phone calls, a number of unread emails calls, text messages, or notifications, etc.). Furthermore, the analog wellness device may measure the number of steps taken by a user attempting to achieve the fitness activity goal, a time period in which the user is inactive, and present this information in an intuitive manner with lower power consumption than devices utilizing a display component.

The analog wellness device may include a fitness activity goal disc and an inactivity disc, each having one or more regions that are visible through windows or cutouts in analog device to function as a gauge to user activity and inactivity, respectively. Although a particular embodiment may be detailed herein, it is to be understood that the regions of each disc may be distinguished in any manner that may be perceived by a user. For instance, the regions may differ in color, texture, pattern or increasing graphics. In embodiments, the fitness activity goal disc and the inactivity disc may be substantially the same color and constructed of a metallic or semi-metallic material and have imprinted or engraved on the upper surface of each a texture in a first region that is distinguishable from a texture in a second region such that the amount of each region of each disc that is visible through a window of the analog wellness device function as a gauge to indicate a proportion of the fitness activity goal that has been met or exceeded or to indicate user inactivity based upon the time period that the user is inactive. In other embodiments, the fitness activity goal disc and the inactivity disc may be substantially the same color and texture and have affixed on the upper surface of each a plurality of graphics (e.g., stars, jewels, etc.) such that the number of graphics within each disc that are visible through a window of the analog wellness device function as a gauge to indicate a proportion of the fitness activity goal that has been met or exceeded or to indicate user inactivity based upon the time period that the user is inactive.

FIG. 1 is an illustration of a block diagram of an exemplary analog wellness system 100 in accordance with an embodiment of the present disclosure. Analog wellness system 100 includes an analog wellness device 102 and one or more external computing devices 150. In an embodiment, analog wellness device 102 and one or more external computing devices 150 may be configured to communicate with one another using any suitable number of wired and/or wireless links (e.g., wired link 161 and/or wireless link 163) in conjunction with any suitable number and type of communication protocols.

In an embodiment, one or more of external computing devices 150 may include any suitable number and/or type of computing devices configured to facilitate user interaction and data exchange with analog wellness device 102. For example, external computing devices 150 may be implemented as a mobile computing device (e.g., smartphone, tablet, laptop, phablet, netbook, notebook, pager, personal digital assistant (PDA), wearable computing device, smart glasses, a smart watch or a bracelet, etc.), an off-the-shelf system to assist a user engage in a physical activity (e.g., an off-the-shelf product configured to assist a user while playing golf) or other suitable type of computing device capable of wired and/or wireless communication (e.g., a desktop computer).

In an embodiment, one or more of external computing devices 150 may facilitate user interaction such as, for example, viewing activity data, viewing inactivity data, viewing a fitness activity goal, viewing and responding to communications (e.g., emails, text messages, etc.), and/or using applications. Communications between one or more of external computing devices 150 and analog wellness device 102 may facilitate the transfer of data between these devices. For example, as further discussed below, data may be transferred from one or more of external computing devices 150 to analog wellness device 102, which may include a threshold number of steps associated with a daily fitness activity goal, a current time, changes to the daily fitness activity goal, a number of missed phone calls, a number of unread emails calls, text messages, or notifications. To provide another example, data may be transferred from analog wellness device 102 to one or more external computing devices 150, which may include a number of steps taken by a user towards accomplishing a daily fitness activity goal, a log of user inactivity, etc., which is also further discussed below.

Analog wellness device 102 may be implemented as any suitable type of wearable device configured to measure and provide user activity in accordance with the embodiments described herein. In an embodiment, analog wellness device 102 may be configured as an analog watch worn by a user. To provide additional examples, analog wellness device 102 may be implemented as a wrist or ankle bracelet, an analog pocket watch, etc.

In an embodiment, analog wellness device 102 may include a communication unit 104, a processor 106, a sensor array 108, a location determining component 109, N number of motors 110.1-110.N, and a memory 118. Analog wellness device 102 may include additional elements such as, for example, power sources, motor controllers, ports, interconnects, etc., which are not described herein for purposes of brevity.

Communication unit 104 may be configured to support any suitable number and/or type of communication protocols to facilitate communications between analog wellness device 102 and one or more of external computing devices 150. Communication unit 104 may be implemented with any suitable combination of hardware and software to facilitate this functionality. For example, communication unit 104 may be implemented with any number of wired and/or wireless transceivers, ports, connectors, etc.

Communication unit 104 may be configured to facilitate communications with various external computing devices 150 using different types of communication protocols. For example, communication unit 104 may communicate with a mobile computing device via a wireless BLUETOOTH communication protocol and with a laptop or a personal computer via a wired universal serial bus (USB) protocol. Communication unit 104 may be configured to support simultaneous or separate communications between two or more of external computing devices 150.

Communication unit 104 may be configured to receive any suitable type of information, which may be provided by analog wellness device 102. In various embodiments, processor 106 may cause analog wellness device 102 to provide information received via communication unit 102, or information that is generated locally via one or more components of analog wellness device 102, which is further discussed below with reference to FIGS. 11-13.

In various embodiments, communication unit 104 may facilitate the receipt of various types of information provided by analog wellness device 102. This information may be based upon the type of external computing devices 150 in which analog wellness device 102 is communicating. For example, if analog wellness device 102 is communicating with a mobile computing device, then communication unit 104 may receive information such as a notification that the mobile computing device has a number of missed calls, the number of these missed calls, a battery level indicator (e.g., low battery), an indication of an incoming call, a number of unread and/or new email messages, a number of new and/or unread text messages, data indicative of one or more emoticons, emoji, graphics, labels, etc.

Additionally or alternatively, information obtained via communication unit 104 may be utilized by processor 106 and provided by analog wellness device 102. For example, processor 106 may cause analog wellness device 102 to indicate information such as a communication status between analog wellness device 102 and one or more external computing devices 150 (e.g., whether analog wellness is connected to a particular device), whether one or more Wi-Fi networks are detected, whether analog wellness device 102 is connected to a Wi-Fi network, etc.

Sensor array 108 may be implemented as any suitable number and type of sensors configured to measure, monitor, and/or quantify a user's motion while wearing analog wellness device 102 as motion data. Sensor array 108 may be advantageously mounted or otherwise positioned within analog wellness device 102 to facilitate these functions. Sensor array 108 may be configured to measure a user's motion and/or to generate motion data continuously or in accordance with any suitable recurring schedule, such as once per every 5 seconds, once per every 10 seconds, once per every 30 seconds, etc.

Examples of suitable sensor types implemented by sensor array 108 may include one or more accelerometers, gyroscopes, perspiration detectors, compasses, speedometers, magnetometers, barometers, thermometers, proximity sensors, light sensors, Hall Effect sensors, electromagnetic radiation sensors (e.g., infrared and/or ultraviolet radiation sensors), humistors, hygrometers, altimeters, biometrics sensors (e.g., heart rate monitors, blood pressure monitors, skin temperature monitors), microphones, etc.

In some embodiments, sensor array 108 may additionally or alternatively facilitate user interaction with analog wellness device 102. For example, sensor array 108 may detect user interactions with analog wellness device 102 such as button presses, a user twisting and/or pressing a crown (e.g., when analog wellness device 102 is implemented as an analog watch), a user shaking analog wellness device 102 to indicate a particular command in accordance with a predetermined motion profile, etc.

Again, information generated locally via one or more components of analog wellness device 102 may be utilized by processor 106 and provided by analog wellness device 102. For example, processor 106 may cause heart rate information obtained via sensor array 108 to be indicated on analog wellness device 102, which is further discussed below with reference to FIG. 13.

To provide another example, processor 106 may cause data to be indicated on analog wellness device 102 related to an activity in which a user in engaged in, which is further discussed below with respect to FIGS. 12A-12C. This information may include, for example, a number of golf strokes, the par for a particular hole a golfer is playing, the direction and/or distance to a golf hole, lay-up information, one or more suggested golf clubs for a particular hole, a front, back, and/or middle distance from the user to a golf green, etc.

Location determining component 109 may be configured to utilize any suitable communications protocol to facilitate determining a geographic location of analog wellness device 102. For example, location determining component 109 may communicate with one or more satellites and/or wireless transmitters in accordance with a Global Navigation Satellite System (GNSS) to determine a geographic location of analog wellness device 102. Wireless transmitters are not illustrated in FIG. 1, but may include, for example, one or more base stations, ground stations, etc.

For example, location determining component 109 may be configured to utilize "Assisted Global Positioning System" (A-GPS), by receiving communications from a combination of base stations, ground stations, and/or satellites. Examples of suitable global positioning communications protocol may include Global Positioning System (GPS), the GLONASS system operated by the Russian government, the Galileo system operated by the European Union, etc.

Motors 110.1-110.N may be configured as any suitable number and/or type of motors to facilitate the embodiments of the disclosure as described herein. One or more of motors 110.1-110.N may receive commands from processor 106 and rotate a number of degrees either clockwise or counterclockwise in response to such commands. Motors 110.1-110.N may be configured to move in any suitable manner, such as continuously or incrementally, for example. In various embodiments, one or more of motors 110.1-110.N may function to, for example, provide quartz movement of watch components such as second, minute, and hour hands and/or to rotate discs to provide a gauge of user activity and inactivity, which is further discussed below. Motors 110.1-110.N may be used to determine the position of and thereby drive the hour, minute and second hands clockwise or counterclockwise.

In embodiments in which one or more motors 110.1-110.N move incrementally, any suitable incremental degree of rotation may be used, such as one degree, two degrees, six degrees, etc. The incremental movement may be based upon the particular application for which a motor is utilized. For example, if one of motors 110.1-110.N is implemented to rotate a second hand, then that motor may rotate incrementally every six degrees to line up with each second tick mark on a watch face. The second hand could also be rotated every two degrees to achieve three ticks per second. To provide another example, if one of motors 110.1-110.N is implemented to rotate an activity or an inactivity disc, which is further discussed below, then that motor may rotate incrementally every two or three degrees to aesthetically align with an even multiple of the incremental second hand movement or other indicators/features on the face.

In an embodiment, motors 110.1-110.N may include the same type of different types of motors. In various embodiments, motors 110.1-110.N may be implemented as any suitable combination of stepper motors, synchronous motors, impulse motors, direct current (DC) motors, off-the-shelf watch motors, etc.

To provide an illustrative example, one of motors 110.1-110.N may be implemented as an off-the-shelf motor configured to facilitate watch movement of one or more hour, minute and/or second hands, while two or more of motors 110.1-110.N may be implemented as stepper motors, for example, which is further discussed below. When one or more of motors 110.1-110.N is implemented as a stepper motor, this may advantageously allow processor 106 to ascertain the position of the stepper motor without the use of an encoder or other type of positional feedback.

Processor 106 may be configured to communicate with one or more of communication unit 104, sensor array 108, one or more of motors 110.1-110.N, and/or memory 118 via one or more wired and/or wireless interconnections, such as any suitable number of data and/or address buses, for example. These interconnections are not shown in FIG. 1 for purposes of brevity.

Processor 106 may be configured to operate in conjunction with one or more of communication unit 104, sensor array 108, one or more of motors 110.1-110.N, and/or memory 118 to process data, to store data to memory 118, to retrieve data from memory 118, to command one or more of motors 110.1-110.N to various angular positions, to read a state and/or position of one or more of motors 110.1-110.N, to receive, process, and/or interpret data from sensor array 108 such as motion data and/or user interactions, to receive data from one or more external computing devices such as daily fitness activity goal data, etc.

Processor 106 may be implemented as any suitable type and/or number of processors, such as a host processor of analog wellness device 102, for example. To provide additional examples, processor 106 may be implemented as an application specific integrated circuit (ASIC), an embedded processor, a central processing unit associated with analog wellness device 102, etc.

In accordance with various embodiments, memory 118 may be a computer-readable non-transitory storage device that may include any suitable combination of volatile (e.g., a random access memory (RAM), or non-volatile memory (e.g., battery-backed RAM, FLASH, etc.). Memory 118 may be configured to store instructions executable on processor 106, such as the various memory modules illustrated in FIG. 1 and further discussed below. These instructions may include machine readable instructions that, when executed by processor 106, cause processor 106 to perform various acts as described herein. Memory 118 may also be configured to store any other suitable data, such as data received from one or more of external computing devices 150 via communication unit 104, data measured, calculated, and/or generated via sensor array 108, daily fitness activity goals, data indicative of user activity and/or user inactivity over a period of time (e.g., daily logs of activity and/or inactivity data), etc.

Timer and synchronization module 119 is a region of memory 118 configured to store instructions, that when executed by processor 106, cause processor 106 to perform various acts in accordance with applicable embodiments as described herein. In an embodiment, timer and synchronization module 119 includes instructions, that when executed by processor 106, cause processor 106 to start, stop, and/or maintain one or more timers and/or real time clocks and/or to facilitate the synchronization of data between analog wellness device 102 and one or more external computing devices.

In an embodiment, processor 106 may execute instructions stored in timer and synchronization module 119 to facilitate one or more functions associated with maintaining a reference time. To provide an example, processor 106 may execute instructions stored in timer and synchronization module 119 to maintain one or more timers to determine a time period of user activity and/or inactivity based upon motion data received from sensor array 108, which is further discussed below. In embodiments, processor 106 may not process the time functions of the watch, which may operate independently from the processor 106 such that the time is set manually by the user and driven by quartz movement. In embodiments, the processor may be operable to determine the time being provided by the watch hands by determining a current position of each watch arm as driven by quartz movement.

Additionally or alternatively, processor 106 may execute instructions stored in timer and synchronization module 119 to maintain a reference time by receiving a current time from one or more computing devices, such as external computing devices 150, for example. In accordance with such an embodiment, processor 106 may execute instructions stored in fitness activity goal calculation module 120 to work in conjunction with communication unit 104 to connect to one of external computing devices 150 to receive an initial time. In this way, analog wellness device may automatically keep track of the time to determine whether goals have been met within specific time periods.

Additionally or alternatively, embodiments include processor 106 executing instructions stored in timer and synchronization module 119 to facilitate two-way communications between analog wellness device 102 and one or more external computing devices 150. Via two-way communications, processor 106 may maintain synchronicity between analog wellness device 102 and one or more external computing devices 150. For example, analog wellness device 102 may send data to one or more external computing devices 150 indicative of user activity and/or user inactivity, whether the user met or exceeded one or more daily goals, a time of day in which a user was active and/or inactive throughout the day, etc.

To provide another example, analog wellness device 102 may receive data from one or more external computing devices 150 such as previous logs of user activity and/or inactivity stored as part of a user profile, records of whether the user met or exceeded one or more daily goals and the corresponding days, a time of day in which a user was active and/or inactive throughout the day, etc. Data used for setting the time, maintaining one or more timers, and/or synchronizing data between analog wellness device 102 and one or more of external computing devices 150 may be stored in memory 118 and/or any other suitable storage device utilized by analog wellness device 102.

Processor 106 may additionally or alternatively work in conjunction with sensor array 108 to initiate one or more functions performed by processor 106 executing instructions stored in timer and synchronization module 119. For example, in embodiments in which analog wellness device 102 is implemented as an analog watch, processor 106 may receive an indication that a watch crown has been pressed by a user, a watch crown has been twisted, a motion profile has been met, etc. In response to the receipt of such an input as indicated by sensor array 108, processor 106 may be configured to initiate communications with one more external computing devices, to set a reference time, to synchronize data, to set a daily fitness activity goal, etc.

Activity goal calculation module 120 is a region of memory 118 configured to store instructions, that when executed by processor 106, cause processor 106 to perform various acts in accordance with applicable embodiments as described herein. In an embodiment, fitness activity goal calculation module 120 includes instructions, that when executed by processor 106, cause processor 106 to determine a fitness activity goal for a certain period of time. For example, the fitness activity goal may be a threshold number of steps to be taken by a user wearing analog wellness device 102 over a one day period, a two day period, a one week period, etc.

In some embodiments, processor 106 may determine the fitness activity goal independently without communicating or receiving data from other external computing devices. In accordance with such embodiments, fitness activity goal calculation module 120 may include instructions specifying a preset, preprogrammed, and/or default fitness activity goal, which may be a threshold number of steps. Processor 106 may read these instructions to determine an initial fitness activity goal, which may remain the same over time, be increased incrementally based upon a user regularly achieving the daily fitness activity goal, be decreased incrementally based upon a user regularly failing to achieve the daily fitness activity goal, etc.

To provide an illustrative example, fitness activity goal calculation module 120 may include instructions specifying an initial fitness activity goal of M steps in a one day period. This number of steps M may be increased over time, for example, when processor 106 determines that a number of days have elapsed in which the daily fitness activity goal has been achieved. In such a case, fitness activity goal calculation module 120 may cause processor 106 to adjust the number of steps to increase M by 5%, by 10%, etc.

In other embodiments, processor 106 may determine a fitness activity goal by receiving data from one or more other external computing devices, such as external computing devices 150, for example. In accordance with such embodiments, fitness activity goal calculation module 120 may include instructions to specify the fitness activity goal as one received from one or more external computing devices.

To provide an illustrative example, a user may use one of external computing devices 150 to access to a user profile and setup an initial fitness activity plan, which may specify a fitness activity goal, conditions upon which to increase the initial daily fitness activity goal, how much to increase the daily fitness activity goal when the conditions are satisfied, how much to decrease the daily fitness activity goal when the conditions are not satisfied, etc. In accordance with such an embodiment, processor 106 may execute instructions stored in fitness activity goal calculation module 120 and work in conjunction with communication unit 104. In doing so, processor 106 may connect to one or more of external computing devices 150 to receive the fitness activity goal.

Step calculation module 122 is a region of memory 118 configured to store instructions, that when executed by processor 106, cause processor 106 to perform various acts in accordance with applicable embodiments as described herein. In an embodiment, step calculation module 122 includes instructions, that when executed by processor 106, cause processor 106 to monitor, track, measure, and/or calculate a user's steps while wearing analog wellness device 102. For example, processor 106 may execute instructions stored in step calculation module 122 to process motion data generated by sensor array 108 and use this data to determine a number of steps taken by the user.

Step calculation module 122 may include instructions to facilitate processor 106 calculating a number of steps in accordance with any suitable techniques based upon the particular type and number of sensors implemented by sensor array 108. For example, sensor array 108 may include a three-axis accelerometer. In such a case, step calculation module 122 may include instructions to facilitate processor 106 to calculate a number of steps based upon motion data generated by sensor array 108 in accordance with x, y, and z-axis accelerometer metrics.

Upon calculating a number of steps, processor 106 may execute instructions stored in step calculation module 122 to store the number of steps in any suitable region of memory 118. The number of steps may be stored in memory 118 as the steps are calculated or at a subsequent time after the steps are calculated, such as a period of time after the user has stopped moving, a predetermined time after the steps are calculated, etc. In various embodiments, processor 106 may store the number of steps in a suitable region of memory 118 correlated with other data such as a time or day when the steps were taken, a frequency of the steps over one or more time periods, a time of day when the daily fitness activity goal was achieved, a time when the daily fitness activity goal was exceeded, the corresponding proportion of the fitness activity goal that was exceeded, etc. Upon storing the calculated number of steps and/or data associated therewith in a suitable region of memory 118, processor 106 may cause one or more of motors 110.1-110.N to rotate a number of degrees to indicate the user's progress towards achieving the daily fitness activity goal, which is further discussed below.

Inactivity calculation module 124 is a region of memory 118 configured to store instructions, that when executed by processor 106, cause processor 106 to perform various acts in accordance with applicable embodiments as described herein. In an embodiment, inactivity calculation module 124 includes instructions, that when executed by processor 106, cause processor 106 to monitor, track, measure, and/or calculate a period of user inactivity while wearing analog wellness device 102.

For example, processor 106 may execute instructions stored in inactivity calculation module 124 to process motion data generated by sensor array 108 and to calculate an inactivity time period, based upon this data, that a user is inactive. Processor 106 may work in conjunction with timer and synchronization module 119 to facilitate this calculation. For example, processor 106 may start a timer each time steps are not being calculated based upon motion data generated via sensor array 108. The timer may be started, for example, when no steps are detected or some threshold amount of time thereafter, such as 5 minutes, 10 minutes, 15 minutes, etc.

In accordance with such embodiments, processor 106 may calculate the inactivity time period as a time period over which no steps are calculated. For example, if no steps are being calculated, then processor 106 may start a timer that accumulates time as long as the user remains inactive. Additionally or alternatively, processor 106 may calculate the time as an accrued time period of inactivity that is increases when no steps are being calculated, but recedes when processor 106 resumes the calculation of steps. To continue the previous example, a user may be inactive for an hour and then walk for a half hour, during which the user's steps are calculated. In addition to processor 106 calculating the number of steps via execution of instructions stored in step calculation module 122, processor 106 may also adjust the inactivity time period from one hour to 30 minutes based upon processor 106 calculating steps being taken by the user for a half hour.

Processor 106 may be configured to command one of motors 110.1-110.N to rotate in one direction to cause the inactivity time period to be presented, which is further discussed below. Then, upon a user engaging in activity resulting in the calculation of steps, processor 106 may be configured to command the motor to rotate in the opposite direction to cause the inactivity time period to be reduced while the user is active. If the user remains active for a time period (i.e., a number of steps are being calculated) equal to the previously accrued inactivity time period, then the presented inactivity time period may be reset to zero. In this way, analog wellness device 102 provides user inactivity feedback as well as user activity feedback, thereby providing an additional incentive for a user to engage in additional activity to reset the presented inactivity time period.

Notifications module 128 is a region of memory 118 configured to store instructions, that when executed by processor 106, cause processor 106 to perform various acts in accordance with applicable embodiments as described herein. In some embodiments, processor 106 may execute instructions stored in notifications module 128 to run one or more local applications and/or to generate data in accordance with the execution of or more local applications, algorithms, processes, etc.

In other embodiments, processor 106 may execute instructions stored in notifications module 128 to process data received from one or more external computing devices 150. In either case, embodiments include notifications module 128 including instructions, that when executed by processor 106, cause processor 106 to determine the various types of information to be provided on analog wellness device 102.

For example, processor 106 may execute instructions stored in notifications module 128 to process information received via communication unit 104 when analog wellness device 102 is communicating with a mobile computing device, as previously discussed. Examples of the types of notifications and information indicated on analog wellness device as a result of the execution of instructions stored in notifications module 128 by processor 106 are further discussed below with reference to FIGS. 11A-11D.

To provide another example, processor 106 may execute instructions stored in notifications module 128 to process data in accordance with a specific application, such as those configured to assist a user while engaging in a particular sport. In an embodiment, this application may assist a user in playing golf. In accordance with such embodiments, processor 106 may execute instructions stored in notifications module 128 to process golf course data, which may be downloaded by analog wellness device 102 via communication unit 104 from one or more of external computing devices 150 and/or otherwise programmed as part of the instructions stored in notifications module 128.

Figure 12A:
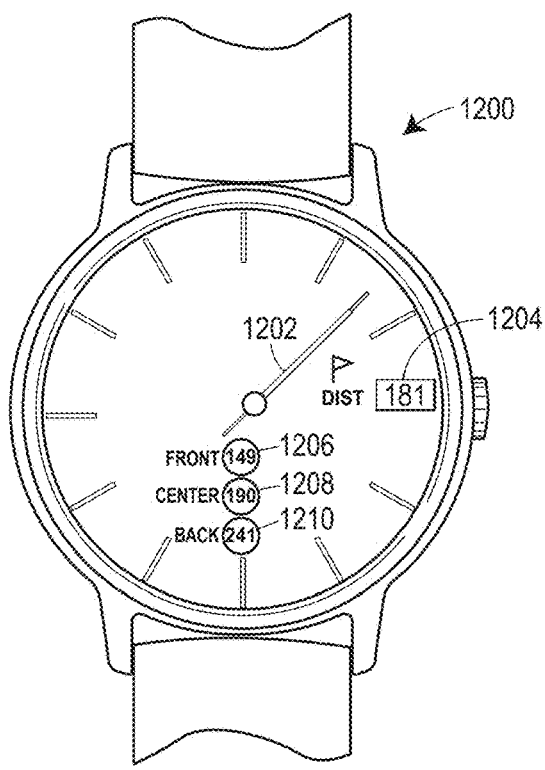
FIG. 12A is an illustration of an exemplary analog watch 1200 indicating golf course navigational information, according to an embodiment.
Figure 12B:
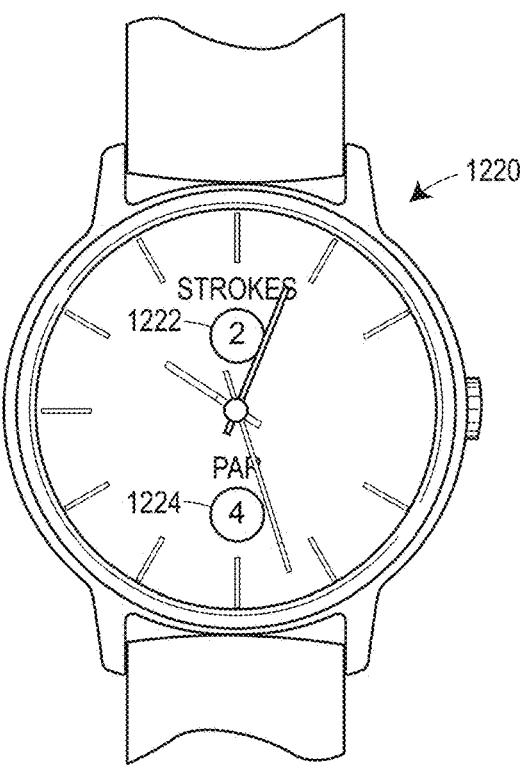
FIG. 12B is an illustration of an exemplary analog watch 1220 indicating golf scoring information, according to an embodiment.
Figure 12C:
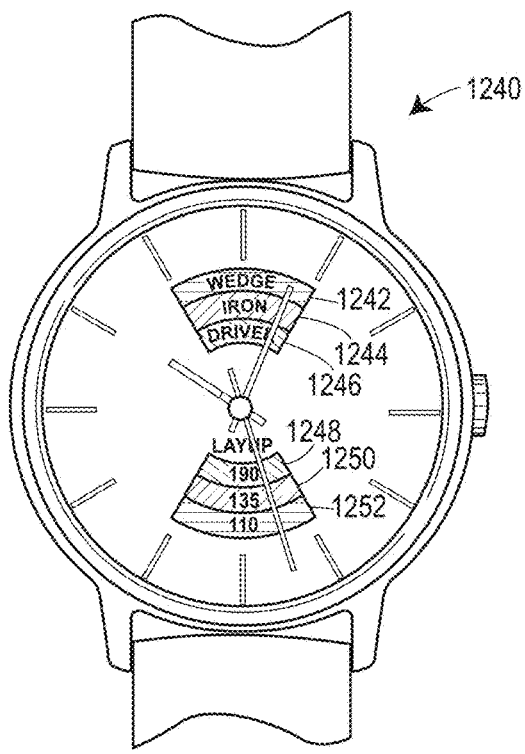
FIG. 12C is an illustration of an exemplary analog watch 1240 indicating golf strategy information, according to an embodiment.

Using the golf course data, processor 106 may execute instructions stored in notifications module 128 to determine the user's position via location determining component 109 with respect to one or more golf course locations, to process motion data generated via sensor array 108 to record a user's golf strokes for one or more holes, to determine a par for one or more golf course holes, to determine a distance and direction from analog wellness device 102 to one or more golf course locations, a front, back, and/or middle distance from analog wellness device 102 to a golf green, a club selection for a particular hole, a resulting lay-up associated with one or more clubs for a particular hole, scoring information, etc., any of which may be provided on analog wellness device 102, which is further discussed below with respect to FIGS. 12A-12C.

To provide yet another example, processor 106 may execute instructions stored in notifications module 128 to process information received via sensor array 108 to provide biometric information such as a user's heart rate, which is further discussed below with reference to FIG. 13.

Motor drive module 126 is a region of memory 118 configured to store instructions, that when executed by processor 106, cause processor 106 to perform various acts in accordance with applicable embodiments as described herein. In an embodiment, motor drive module 126 includes instructions, that when executed by processor 106, cause processor 106 to determine a number of degrees or steps to command one or more motors 110.1-110.N to rotate based upon various types of data.

For example, processor 106 may execute instructions stored in motor drive module 126 to command one or more of motors 110.1-110.N to rotate respective hour, minute, and/or second hands to provide time in an analog fashion or other desired functions such as heart-rate meter or compass. To provide another example, processor 106 may execute instructions stored in motor drive module 126 to calculate a number of degrees or steps to rotate one or more motors 110.1-110.N to rotate respective multicolored discs to present user activity and/or user inactivity.

To provide yet another example, processor 106 may execute instructions stored in motor drive module 126 to calculate a number of degrees or steps to rotate one or more motors 110.1-110.N to rotate other discs or the watch hands. Again, the discs may include different colors, textures, labels, text, emoticons, emoji, symbols, indicia, graphics, etc., to present other types of information to a user, which is further discussed below with respect to FIGS. 11-13.

Processor 106 may be configured to calculate a proportion of the fitness activity goal that has been met based upon a calculated number of steps and the calculated fitness activity goal. Using this proportion, processor 106 may command the respective one or motors 110.1-110.N to rotate a number of steps or degrees.

To provide an illustrative example, one of motors 110.1-110.N may be a fitness activity goal motor and, as the fitness activity goal motor rotates, may cause a first disc with multiple distinct regions, such as different colors, coupled to a shaft of the fitness activity goal motor to also rotate. Likewise, another one of motors 110.1-110.N may be an inactivity motor and, as the inactivity motor rotates, may cause a second disc with multiple distinct regions, such as different colors, coupled to a shaft of the inactivity motor to also rotate.

Continuing this example, analog wellness device 102 may have cutouts or windows such that various colored regions of the first and second multicolored discs may be viewed as each of the fitness activity goal motor and the inactivity motor rotates. If a user's fitness activity goal is 2000 steps and the current steps calculation is 500 steps, then processor 106 may command the fitness activity goal motor to rotate a number of degrees such that 25% of one color on the first multicolored disc is visible while 75% of another color is visible through the cutouts or windows. In this way, as the fitness activity goal motor and the inactivity motor each rotate, the amount of various colors visible through windows or cutouts in analog device 102 may function as a gauge to user activity and inactivity.

In various embodiments, processor 106 may calculate a number of degrees and/or steps to command a fitness activity goal motor and a inactivity motor to rotate in accordance with any suitable sampling rate and/or schedule. For example, processor 106 may calculate a number of degrees and/or steps and command a fitness activity goal motor and/or a inactivity motor to rotate the number of calculated degrees and/or steps every 5 seconds, every 10 seconds, every 30 seconds, etc. In this way, analog wellness device 102 may present user activity data and/or inactivity data in real-time or near real-time.

Additionally or alternatively, processor 106 may execute instructions stored in motor drive module 126 to reset one or more of motors 110.1-110.N upon expiration of the time period associated with the fitness activity goal, thereby starting the process of monitoring user activity and inactivity over again for the next time period. For example, a fitness activity goal motor and a inactivity motor may each have a respective starting, home, and/or default position. At the beginning of each time period associated with the fitness activity goal, the fitness activity goal motor and the inactivity motor may each reset or return to these home positions.

In an embodiment, processor 106 may determine the end of the time period associated with the fitness activity goal by executing instructions stored in timer and synchronization module 119. For example, if the fitness activity goal is a one day period of time, then processor 106 may determine when a 24 hour period has elapsed as the expiration of the time period associated with the fitness activity goal, and reset the fitness activity goal motor and the inactivity motor accordingly.

To provide another example, processor 106 may determine the end of the time period associated with the fitness activity goal by processing motion data generated by sensor array 108. For example, if motion data generated by sensor array 108 indicates that analog wellness device 102 is not moving for a threshold period of time (e.g., 4 hours, 6 hours, etc.) then processor 106 may ascertain that the user is likely asleep, and reset the fitness activity goal motor and the inactivity motor accordingly.

Similar actions may be performed based upon any suitable input from one or more components of analog wellness device 102, such as analog wellness device charging for a threshold period of time, an alarm set on the watch going off (when analog wellness device 102 is so implemented), the user moving analog wellness device 102 in accordance with a predetermined motion profile, etc.

Figure 2:
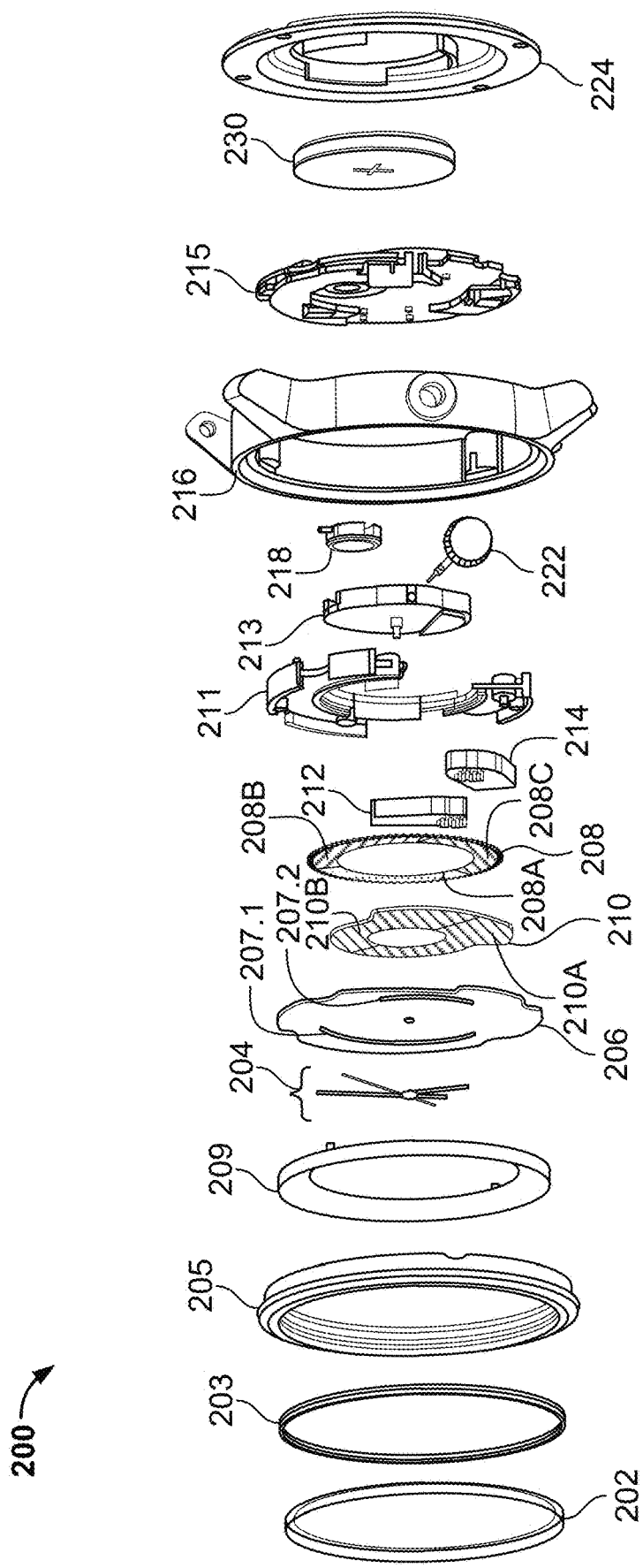
FIG. 2 is an illustration of an exploded view of an exemplary analog watch 200 in accordance with an embodiment of the present disclosure.

FIG. 2 is an illustration of an exploded view of an exemplary analog watch 200 in accordance with an embodiment of the present disclosure. In an embodiment, analog watch 200 is an implementation of analog wellness device 102, as shown in FIG. 1.

Analog watch 200 may include a glass cover 202, an i-ring 203, time-keeping hands 204, a bezel 205, a watch face 206, a fitness activity goal multicolored disc 208, a watch face bezel 209, an inactivity multicolored disc 210, a disk retention fixture 211, a fitness activity goal motor 212, a quartz movement 213, an inactivity motor 214, a printed circuit board (PCB) 215, a watch housing 216, a power connection 218, a crown/button 222, a rear case 224, and a battery 230. Analog watch 200 may include additional or fewer components as shown in FIG. 2. For example, the second hand may be omitted, additional crowns and/or buttons may be added, etc.

Quartz movement 213 may be coupled to time-keeping hands 204 and configured to move time-keeping hands 204 in accordance with an analog watch movement. For example, quartz movement 213 may be implemented as an off-the-shelf quartz clock.

PCB 215 may include one or more hardware components configured to facilitate the operation of analog watch 200, some of which are not shown in FIG. 2 for purposes of brevity. Using the example of analog watch 200 as an implementation of analog wellness device 102, PCB 215 may incorporate and/or house components such as communication unit 104, processor 106, sensor array 108, one or more ports, various interconnections between components, memory 118, one or more motors 110.1-110.N, etc.

In an embodiment, power connection 218 may be electrically coupled to battery 230 via any suitable number and/or type of connections (e.g., via PCB 215). In some embodiments, power connection 218 may provide power, via its coupling to battery 230, to one or more of quartz movement 213, fitness activity goal motor 212, inactivity motor 214, and/or one or more regions of PCB 215. In other embodiments, PCB 215, fitness activity goal motor 212, and/or inactivity motor 214 may be powered via one or more electrical couplings to battery 230, which may or may not utilize power connection 218.

Fitness activity goal motor 212 and inactivity motor 214 may be mounted and/or affixed to PCB 215 and coupled to a processor mounted on PCB 215 (e.g., processor 106, as shown in FIG. 1) such that fitness activity goal motor 212 and inactivity motor 214 may receive commands from the processor. These commands may cause fitness activity goal motor 212 and inactivity motor 214 to rotate, thereby rotating fitness activity goal multicolored disc 208 and inactivity multicolored disc 210, respectively. In an embodiment, fitness activity goal motor 212 and inactivity motor 214 may be implementations of one or more motors 110.1-110.N, as shown in FIG. 1.

Fitness activity goal multicolored disc 208 may have any suitable number of different regions, which may be regions of different colors, in any suitable proportion. In the example shown in FIG. 2, fitness activity goal multicolored disc 208 includes three colored regions 208A-C laid out in equal proportion. Similarly, inactivity multicolored disc 210 may have any suitable number of different colored regions, which may be any color and laid out on inactivity multicolored disc 210 in any suitable proportion. In the example shown in FIG. 2, inactivity multicolored disc 210 includes two colored regions 210A-B laid out in equal proportion.

As shown in FIG. 2, watch face 206 may include windows 207.1 and 207.2. Windows 207.1 and 207.2 may be cutouts in watch face 206 or translucent regions thereof. Thus, as fitness activity goal multicolored disc 208 is rotated by fitness activity goal motor 212, different colored regions 208A-C are visible through window 207.1. Likewise, as inactivity multicolored disc 210 is rotated by inactivity motor 214, different colored regions 210A-B are be visible through window 207.2.

In an embodiment, colored region 208A may be indicative of the fitness activity goal not being met, such that the entirety of colored region 208A is visible through window 207.1 prior to any steps being calculated—or when fitness activity goal motor 212 is rotated to its home position. Thus, fitness activity goal multicolored disc 208 and fitness activity goal motor 212 may be mounted and positioned within analog watch 200 such only colored region 208A is visible through window 207.1 at the start of a time period associated with a fitness activity goal, such as the beginning of the day when the fitness activity goal is a one day period, for example.

Continuing to use a daily fitness activity goal as an example, colored region 208B may be indicative of the fitness activity goal being met such that the proportion of colored region 208B to colored region 208A that is visible through window 207.1 is the same proportion of the fitness activity goal that has been met. For example, if the daily fitness activity goal is 2000 steps and 1500 steps have been calculated, fitness activity goal multicolored disc 208 may be rotated such that window 207.1 would show 25% of colored region 208A and 75% of colored region 208B. In other words, fitness activity goal multicolored disc 208 and fitness activity goal motor 212 may be mounted and positioned within analog watch 200 such that only colored region 208B is visible through window 207.1 when the number of threshold steps associated with the fitness activity goal is met but not exceeded.

Further continuing to use the daily fitness activity goal as an example, colored region 208C may be indicative of the fitness activity goal being exceeded, such that the proportion of colored region 208C to colored region 208B that is visible through window 207.1 is the same proportion of the fitness activity goal that has been exceeded. For example, if the daily fitness activity goal is 2000 steps and 2500 steps have been calculated (125% of the daily fitness activity goal), then window 207.1 would show 75% of colored region 208B and 25% of colored region 208C. In other words, fitness activity goal multicolored disc 208 and fitness activity goal motor 212 may be mounted and positioned within analog watch 200 such that only colored region 208C is visible through window 207.1 when the fitness activity goal is exceeded by some maximum amount, such as 200%, for example. In embodiments, once the multicolored disc 210 has presented all available sections to the maximum percentage of goal (e.g. 200% of goal). The multicolored disc 210 may rotate all the way back to the 0% or starting position to continue to present activity or inactivity progress.

In an embodiment, inactivity multicolored disc 210 has two different equally distributed colored regions 210A-B, one for each half of multicolored disc 210. In accordance with such an embodiment, colored region 210A may be indicative of no inactivity time, such that the entirety of colored region 210A is visible through window 207.2 at the start of a time period associated with the fitness activity goal—or when inactivity motor 214 is rotated to its home position. Thus, inactivity multicolored disc 210 and inactivity motor 214 may be mounted and positioned within analog watch 200 such only colored region 210A is visible through window 207.2 at the start of a time period associated with an fitness activity goal, such as the beginning of the day when the fitness activity goal is a one day period, for example.

Colored region 210B may be indicative of a period of inactivity time such that the proportion of colored region 210A to colored region 210B shown in window 207.2 allows for a time measurement to be determined. For example, if window 207.2 is scaled to a maximum period of inactivity time of two hours, then one hour of inactivity time would be represented in window 207.2 when 50% of colored region 210A and 50% of colored region 210B are each shown. In other words, inactivity multicolored disc 210 and inactivity motor 214 may be mounted and positioned within analog watch 200 such that only colored region 210B is visible through window 207.2 when the maximum period of inactivity time shown in window 207.2 has been met or exceeded.

In various embodiments, windows 207.1 and 207.2 may have any suitable shape, size, and/or position within watch face 206. In an embodiment, windows 207.1 and 207.2 are shaped as arcs having equal radii from the center of watch face 206, thereby being concentric with the center of watch face 206. In accordance with embodiments in which window 207.1 and/or window is arc-shaped, each of window 207.1 and/or window 207.2 may have any suitably sized central angle. In an embodiment, window 207.1 may have an associated central angle of 120 degrees, such that window 207.1 sweeps through one-third of circular watch face 206. In various embodiments, window 207.2 may have a central angle that is proportional to the central angle of window 207.1 and/or a multiple of five-degree increments such that the arc-lengths align with the numbers of watch face 206.

Fitness activity goal multicolored disc 208 and inactivity multicolored disc 210 may have any suitable shape such that, when each is rotated, the colors of each respective disc are visible only through the window associated with each multicolored disc. For example, inactivity multicolored disc 210 may be shaped as a partial disc, as shown in FIG. 2, such that no region of inactivity multicolored disc 210 is visible through window 207.1 even when inactivity multicolored disc 210 in fully rotated or "railed" in either direction.

In accordance with an embodiment, windows 207.1 and 207.2 are positioned such that the bottom region of each window 207.1 and 207.2 are aligned with one another, as shown in FIG. 2. However, windows 207.1 and 207.2 may be positioned in any suitable manner on watch face 206. For example, windows 207.1 and 207.2 may be positioned centered about the horizontal axis of watch face 206, positioned such that the upper regions are aligned with each other, etc.

To provide additional examples, windows 207.1 and 207.2 may be shaped as straight horizontal lines, as angular lines, as full circles concentric with one another, etc. The shape of fitness activity goal multicolored disc 208 and inactivity multicolored disc 210 may be modified from those shown in FIG. 2 to accommodate the shapes of windows 207.1 and 207.2. For example, if windows 207.1 and 207.2 are implemented as concentric circles, fitness activity goal multicolored disc 208 and inactivity multicolored disc 210 may be ring shaped. To provide another example, if windows 207.1 and 207.2 are implemented as straight or angular lines, fitness activity goal multicolored disc 208 and inactivity multicolored disc 210 may be replaced with colored ribbons, colored belts, etc.

Although three colored regions 208A-C and two colored regions 210A-B are shown in FIG. 2, embodiments include multicolored disc 208 and/or multicolored disc 210 implementing any suitable number of colored regions and/or any suitable scaling techniques. For example, multicolored disc 208 could include a fourth colored region to indicate the daily fitness activity goal being exceeded by 200% to 300%. To provide another example, multicolored disc 208 may include unequally colored regions to indicate different proportions of the fitness activity goal that has been met or exceeded.

Furthermore, although FIG. 2 illustrates analog watch 200 as including two windows 207.1 and 207.2, embodiments include watch face 206 including any suitable number of windows. In an embodiment, only one of either window 207.1 or 207.2 may be implemented. In accordance with such an embodiment, some motors and multicolored discs as shown in FIG. 2 may be omitted. For example, analog watch 200 may include window 207.1, fitness activity goal motor 212, and goal multicolored disc 208, but not include window 207.2, inactivity motor 214, and inactivity multicolored disc 210.

In various embodiments, crown/button 222 may be configured to facilitate user interaction with analog watch 200. For example, a user may pull out and/or twist crown/button 222 to set a time and/or date of analog watch 200, which may be in accordance with traditional watch-setting techniques. To provide another example, a user may press crown/button 222, hold in crown/button 222, etc., to initiate data synchronization, to receive an initial fitness activity goal, and/or to receive an initial time used to set analog watch 200, as previously discussed with respect to FIG. 1.

FIG. 3 is an illustration 300 of two exemplary multicolored discs used to indicate a user's activity and inactivity, according to an embodiment. Illustration 300 is a top-down view that shows a goal multicolored disc 302 and an inactivity multicolored disc 304. In an embodiment, goal multicolored disc 302 and inactivity multicolored disc 304 are implementations of goal multicolored disc 208 and inactivity multicolored disc 210, as shown in FIG. 2. Similar to goal multicolored disc 208 and inactivity multicolored disc 210, in the example shown in FIG. 3, goal multicolored disc 302 has three different colored portions 302A-C, while inactivity multicolored disc 304 has two different colored portions 304A-B.

As shown in FIG. 3, the outside of each of goal multicolored disc 302 and inactivity multicolored disc 304 has teeth to mesh with gears 306 and 308, respectively. In an embodiment, gears 306 and 308 are coupled to a shaft that is rotated by their respective motors 350 and 352, which may be implementations of fitness activity goal motor 212 and inactivity motor 214, respectively, for example, as shown in FIG. 2. In this way, when a processor (e.g., processor 106) commands each respective motor to rotate a number of degrees or steps, gear 306 and/or gear 308 rotates, and in turn rotates goal multicolored disc 302 and inactivity multicolored disc 304, respectively, in the opposite direction.

Referring back to FIG. 1, instructions stored in motor drive module 126 may facilitate the compensation of counter-rotation of goal multicolored disc 302 and inactivity multicolored disc 304 to the rotation of gear 306 and/or gear 308, respectively, such that goal multicolored disc 302 and inactivity multicolored disc 304 rotate in the desired direction. Additionally or alternatively, instructions stored in motor drive module 126 may account for the gear ratio between each of gears 306 and 308 and goal multicolored disc 302 and inactivity multicolored disc 304, respectively, such that goal multicolored disc 302 and inactivity multicolored disc 304 rotate by the desired number of degrees or steps.

Although FIG. 3 illustrates goal multicolored disc 302 and inactivity multicolored disc 304 being driven with gears 306 and 308 coupled to outside teeth of each of goal multicolored disc 302 and inactivity multicolored disc 304, embodiments include gears 306 and 308 being coupled to goal multicolored disc 302 and inactivity multicolored disc 304, respectively, in any suitable manner and/or configuration to facilitate the rotation of goal multicolored disc 302 and inactivity multicolored disc 304. For example, goal multicolored disc 302 and inactivity multicolored disc 304 may be ring-shaped or notched and driven from an inner location, screw-driven, etc.

In the following FIGS. 4A-4E, an analog watch 400 is illustrated indicating various states of user activity and user inactivity. In an embodiment, analog watch 400 may be an implementation of analog wellness device 102 or analog watch 200, as shown in FIGS. 1 and 2, respectively. Furthermore, in each of FIGS. 4A-4E, analog watch 400 presents user activity in window 402, which may correspond to window 207.1, for example, as shown in FIG. 2, in an embodiment. Similarly, analog watch 400 may indicate user inactivity in window 404, which may correspond to window 207.2, for example, as shown in FIG. 2, in an embodiment.

Analog watch 400 also includes a suitable label for each of windows 402 and 404. As shown in each of FIGS. 4A-4E, the side of window 402 is labeled with tick marks indicating a percentage of a user's progress towards a fitness activity goal from 0% to 100%. Thus, the proportion of colors presented or visible in window 402 may function as a gauge to allow a user to view progress towards meeting or exceeding a fitness activity goal.

Window 404 may also have an associated label, numbers, or indicators indicative of a period of inactivity. For instance, as shown in each of FIGS. 4A-4E, window 404 is labeled with tick marks indicating a period of inactivity time from 0 to 2 hours. Thus, the proportion of colors presented or visible in window 404 may function as a gauge to allow a user to view accrued inactivity time.

FIGS. 4A-4E illustrate exemplary labels for windows 402 and 404. Again, any suitable scale may be implemented by analog watch 400 and reflected in the labels accordingly. For example, window 402 may include a label indicating a user fitness activity goal progress of 0% to 150%. To provide another example, window 404 may include a label indicating a user inactivity of 0 to 1 hour, 0 to 4 hours, etc.

FIG. 4A is an illustration of an exemplary analog watch 400 registering no steps being taken by a user and no inactivity time, according to an embodiment. As shown in FIG. 4A, each of windows 402 and 404 only show a single color. For window 402, color 403A may correspond to a colored region of a multicolored disc representing the fitness activity goal not being met. In an embodiment, color 403A, which is visible through window 402, may correspond to one colored region of a multicolored disc (e.g., colored region 208A of fitness activity goal multicolored disc 208, as shown in FIG. 2).

Similarly, for window 404, color 405A may correspond to a colored region of a multicolored disc representing no accrual of inactivity time. In an embodiment, color 405A, which is visible through window 404, may correspond to one colored region of a multicolored disc (e.g., colored region 210A of inactivity multicolored disc 210, as shown in FIG. 2).

FIG. 4B is an illustration of an exemplary analog watch 400 indicating a proportion of steps taken by a user towards accomplishing a fitness activity goal and no inactivity time, according to an embodiment. As shown in FIG. 4B, window 402 shows color 403A and color 403B. Color 403B may correspond to a colored region of a multicolored disc representing the fitness activity goal being met. In an embodiment, color 403B, which is visible through window 402, may correspond to one colored region of a multicolored disc (e.g., colored region 208B of fitness activity goal multicolored disc 208, as shown in FIG. 2).

The proportion of color 403A to 403B may function as a gauge to indicate the proportion of the fitness activity goal a user has met based upon a calculated number of steps. Using the label on window 402, FIG. 4B indicates that a user has achieved approximately 65% of the fitness activity goal, which corresponds to the transition between color 403A and color 403B within window 402. The example shown in FIG. 4B assumes that the user has been active and no period of inactivity has accrued between the time period associated with FIG. 4A and FIG. 4B, which is reflected in window 404 of FIG. 4B presenting only color 405A, which remains unchanged from FIG. 4A.

FIG. 4C is an illustration of an exemplary analog watch 400 indicating a proportion of steps taken by a user towards accomplishing a fitness activity goal and some inactivity time, according to an embodiment. The example shown in FIG. 4C assumes that the user was inactive between the time period associated with FIG. 4B and FIG. 4C. That is, the user was inactive after taking the steps calculated and presented in FIG. 4B. Thus, colors 403A and 403B are visible in window 402 in the same proportions as shown in FIG. 4B.

However, window 404 now shows color 405A and color 405B. Color 405B may correspond to a colored region of a multicolored disc representing the fitness activity goal being met. In an embodiment, color 405B may correspond to one colored region of a multicolored disc (e.g., colored region 210B of inactivity multicolored disc 210, as shown in FIG. 2). Using the label on window 404, FIG. 4C indicates that a user has been inactive for approximately 1.3 hours, which corresponds to the transition between color 405A and color 405B within window 404.

Figure 4D:
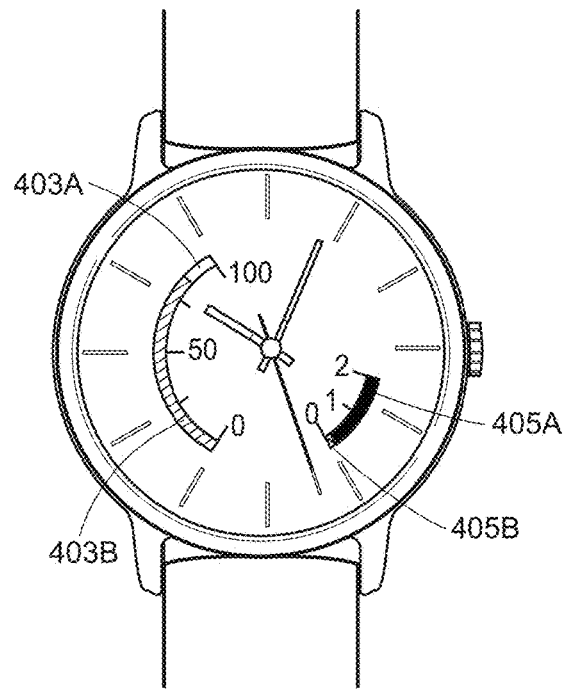
FIG. 4D is an illustration of an exemplary analog watch 400 indicating an increase from FIG. 4C of the proportion of steps taken by a user towards accomplishing the fitness activity goal and a corresponding reduction in inactivity time, according to an embodiment.

FIG. 4D is an illustration of an exemplary analog watch 400 indicating an increase from FIG. 4C of the proportion of steps taken by a user towards accomplishing the fitness activity goal and a corresponding reduction in inactivity time, according to an embodiment. The example shown in FIG. 4D assumes that the user began taking steps after the period of inactivity calculated and presented in FIG. 4C, which yields two results.

First, window 402 indicates the additional calculated steps due to the user's activity by the increased amount of color 403B and the decreased amount of color 403A that are visible in window 402. Second, window 404 indicates a decrease in user inactivity time by the increased amount of color 405A and the decreased amount of color 405B that are visible in window 404.

Figure 4E:
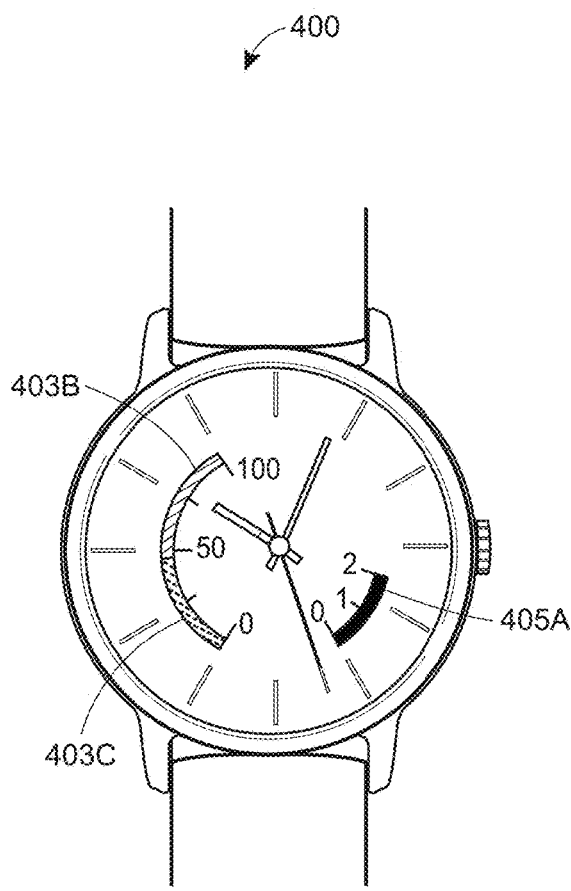
FIG. 4E is an illustration of an exemplary analog watch 400 indicating a proportion of steps taken by a user exceeding a fitness activity goal and no inactivity time, according to an embodiment.

FIG. 4E is an illustration of an exemplary analog watch 400 indicating a proportion of steps taken by a user exceeding a fitness activity goal and no inactivity time, according to an embodiment. As shown in FIG. 4E, window 402 shows color 403B and a color 403C. Color 403C may correspond to a colored region of a multicolored disc representing the fitness activity goal being exceeded. In an embodiment, color 403C may correspond to one colored region of a multicolored disc (e.g., colored region 208C of fitness activity goal multicolored disc 208, as shown in FIG. 2).

The proportion of color 403B to 403C may function as a gauge to indicate the proportion of the fitness activity goal a user has exceeded based upon the calculated number of steps. Using the label on window 402, FIG. 4E indicates that a user has exceeded the fitness activity goal by approximately 40%, which corresponds to the transition between color 403B and color 403C within window 402.

The example shown in FIG. 4E assumes that the user has been active during the time between FIGS. 4D and 4E, which is reflected in window 404 of FIG. 4E presenting only color 405A and none of color 405B, which previously was presented in FIG. 4D.

Figure 5:
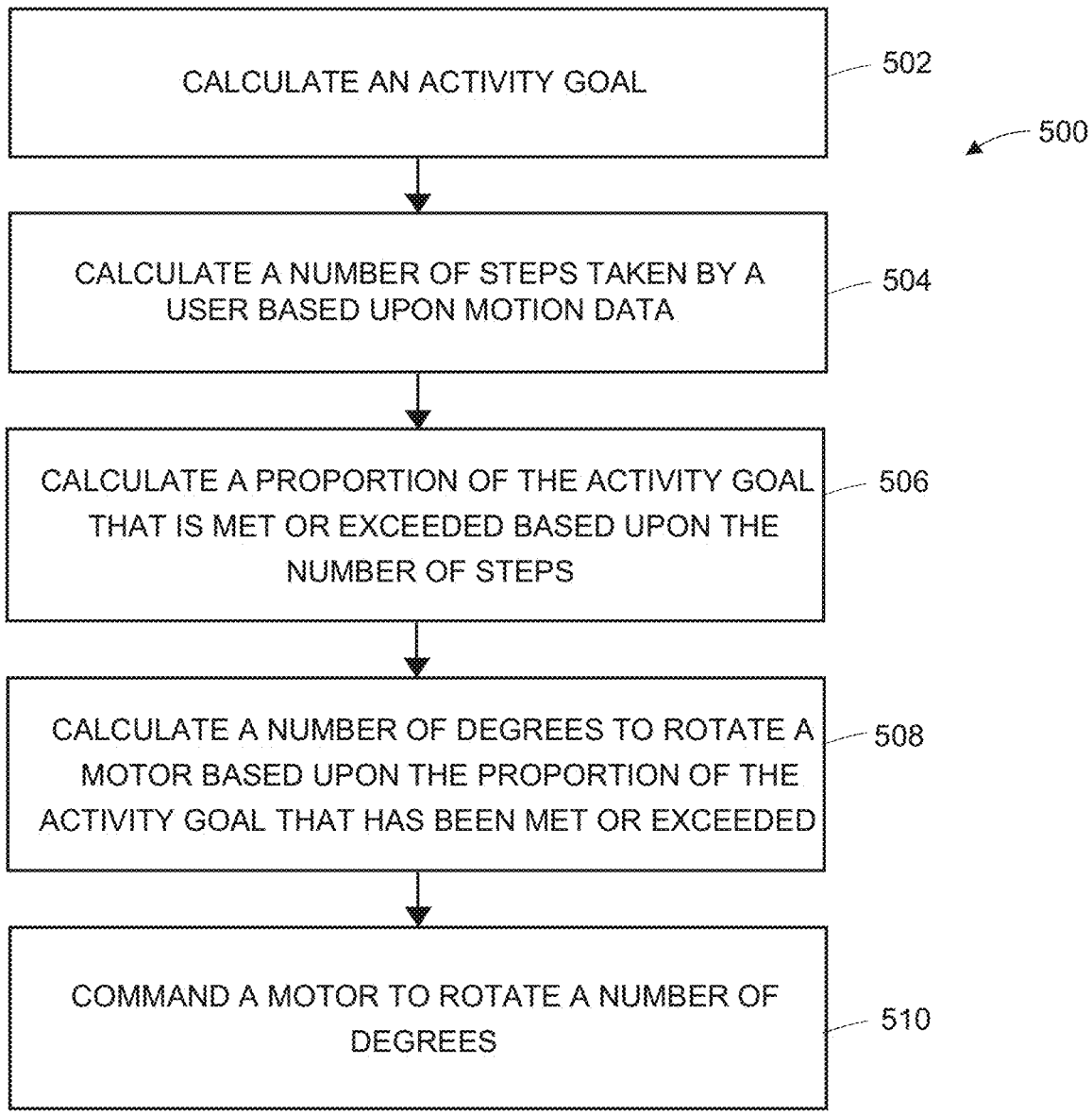
FIG. 5 illustrates a method flow 500, according to an embodiment.

FIG. 5 illustrates a method flow 500, according to an embodiment. In an embodiment, one or more regions of method 500 (or the entire method 500) may be implemented by any suitable device. For example, one or more regions of method 500 may be performed by analog wellness device 102, as shown in FIG. 1. To provide another example, one or more regions of method 500 may be performed by analog watch 200, as shown in FIG. 2.

In an embodiment, method 500 may be performed by any suitable combination of one or more processors, applications, algorithms, and/or routines, such as processor 106 executing instructions stored in one or more of timer and synchronization module 119, fitness activity goal calculation module 120, step calculation module 122, inactivity calculation module 124, and/or motor drive module 126, for example, as shown in FIG. 1.

Method 500 may start when one or more processors calculate a fitness activity goal (block 502). This fitness activity goal may be calculated by the one or more processors independently (block 502) or received from an external computing device (e.g., one or more external computing devices 150, as shown in FIG. 1) (block 502).

Method 500 may include one or more processors calculating a number of steps taken by a user based upon motion data (block 504). This motion data may include, for example, data received from a one or more sensors (e.g., accelerometers), such as sensor array 108, for example, as shown in FIG. 1 (block 504).

Method 500 may include one or more processors calculating a proportion of the fitness activity goal that has been met or exceeded (block 506) using the calculated number of steps (block 504). This may include, for example, calculating a ratio between the calculated number of steps (block 504) and the calculated fitness activity goal (block 502).

Method 500 may include one or more processors calculating a number of degrees to rotate a motor (block 508) based upon the proportion of the fitness activity goal that has been met or exceeded (block 506). The motor may include, for example, fitness activity goal motor 212, as shown in FIG. 2 (block 508). This calculation may compensate for motor gearing, the determination of a number of motor steps (if the motor is implemented as a stepper motor), etc., such that the multicolored disc coupled to the motor presents the appropriate color amount based upon the proportion of the fitness activity goal that has been met or exceeded (block 508).

Method 500 may include one or more processors commanding a motor to rotate a number of degrees (block 510) calculated based upon the proportion of the fitness activity goal that has been met or exceeded (block 508). This may include, for example, sending a command to a stepper motor indicating a number of steps and a direction of rotation (block 510).

Figure 6:
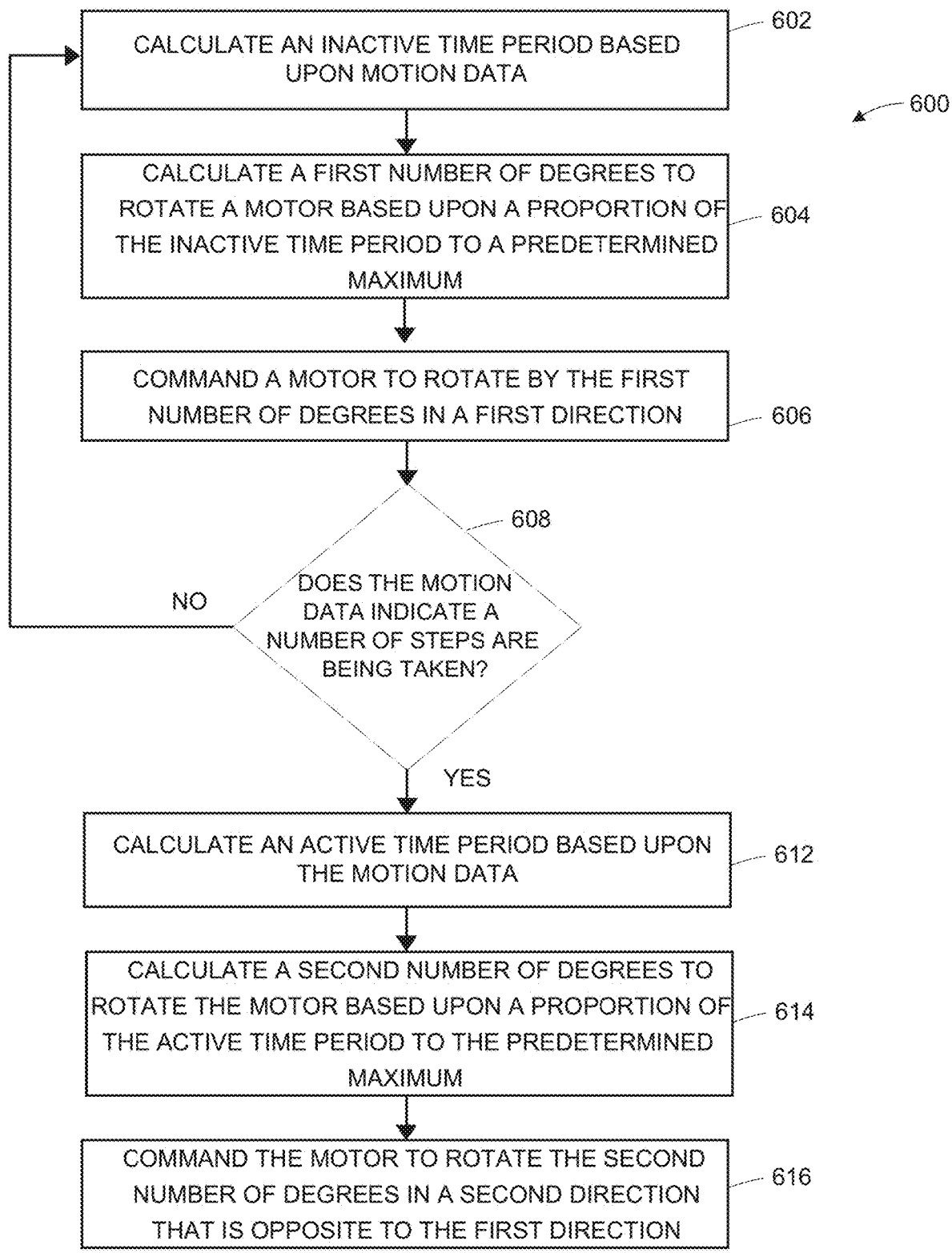
FIG. 6 illustrates a method flow 600, according to an embodiment.

FIG. 6 illustrates a method flow 600, according to an embodiment. In an embodiment, one or more regions of method 600 (or the entire method 600) may be implemented by any suitable device. For example, one or more regions of method 600 may be performed by analog wellness device 102, as shown in FIG. 1. To provide another example, one or more regions of method 600 may be performed by analog watch 200, as shown in FIG. 2.

In an embodiment, method 600 may be performed by any suitable combination of one or more processors, applications, algorithms, and/or routines, such as processor 106 executing instructions stored in one or more of timer and synchronization module 119, fitness activity goal calculation module 120, step calculation module 122, inactivity calculation module 124, and/or motor drive module 126, for example, as shown in FIG. 1.

Method 600 may start when one or more processors calculate an inactive time period based upon motion data (block 602). This motion data may include, for example, data received from one or more sensors (e.g., accelerometers), such as sensor array 108, for example, as shown in FIG. 1 (block 602). The inactive time period may be calculated by referencing one or more timers that are started upon a threshold period of time in which the motion data indicates a lack of motion. This may include, for example, motion data metrics being less than one or more respective threshold values (block 602) for a threshold period of time.

Method 600 may include one or more processors calculating a first number of degrees to rotate a motor based upon a proportion of the calculated inactive time period (block 602) to a predetermined maximum (block 604). This predetermined maximum may correspond to a maximum inactivity time period that may be presented on an analog watch, such as 2 hours, 3 hours, etc., as shown by the accompanying label for windows 404 of FIGS. 4A-4E, for example (block 604).

The motor may include, for example, inactivity motor 214, as shown in FIG. 2 (block 604). This calculation may compensate for motor gearing, the determination of a number of motor steps (if the motor is implemented as a stepper motor), etc., such that the multicolored disc coupled to the motor presents the appropriate color amount based upon the accrued inactivity time period (block 604).

Method 600 may include one or more processors commanding a motor to rotate a first number of degrees in a first direction (block 606), which may be based upon the calculated proportion of the inactive time period to the predetermined maximum (block 604). This may include, for example, sending a command to a stepper motor indicating a number of steps and a direction of rotation (block 606).

Method 600 may include one or more processors determining whether the motion data indicates that a number of steps are being taken (block 608). This may include, for example, one or more processors determining that the motion data indicates that a threshold number of steps (e.g., 25, 50, 100, etc.) have been calculated over a threshold period of time (e.g., 1 minute, 3 minutes, 5 minutes, etc.). If so, method 500 may continue to calculate an active time period based upon the motion data (block 612). Otherwise, method 500 may revert back to calculating the inactive time period, for example, by maintaining a running timer that accrues inactivity time (block 602).

Method 600 may include one or more processors calculating an active time period based upon the motion data (block 612). This may include, for example, starting a timer (block 612) when it is determined that the motion data indicates that a threshold number of steps have been calculated over a threshold period of time (block 608) and stopping the timer when steps are no longer being calculated (block 612). This may also include, for example, if the timer continues to run due to continued steps being calculated, periodically referencing the timer to calculate the active time period in accordance with any suitable sampling rate (e.g., every 15 seconds, 30 seconds, 1 minute, etc.) (block 612).

Method 600 may include one or more processors calculating a second number of degrees to rotate the motor based upon a proportion of the calculated active time period (block 612) to the predetermined maximum (block 614). For example, if the inactivity time period is one hour, the predetermined maximum is two hours, and the active time period is 15 minutes, the second number of degrees may be calculated, for example, based upon the proportion of 15 minutes to 2 hours (block 614).

Method 600 may include one or more processors commanding the motor to rotate the second number of degrees in a second direction that is opposite to the first direction (block 616). This may include, for example, sending a command to a stepper motor indicating a number of steps and a direction of rotation so that less of a color indicating the inactivity time period is presented or visible, as shown in the transition of analog watch 400 from FIG. 4C to FIG. 4D (block 616).

Figure 7:
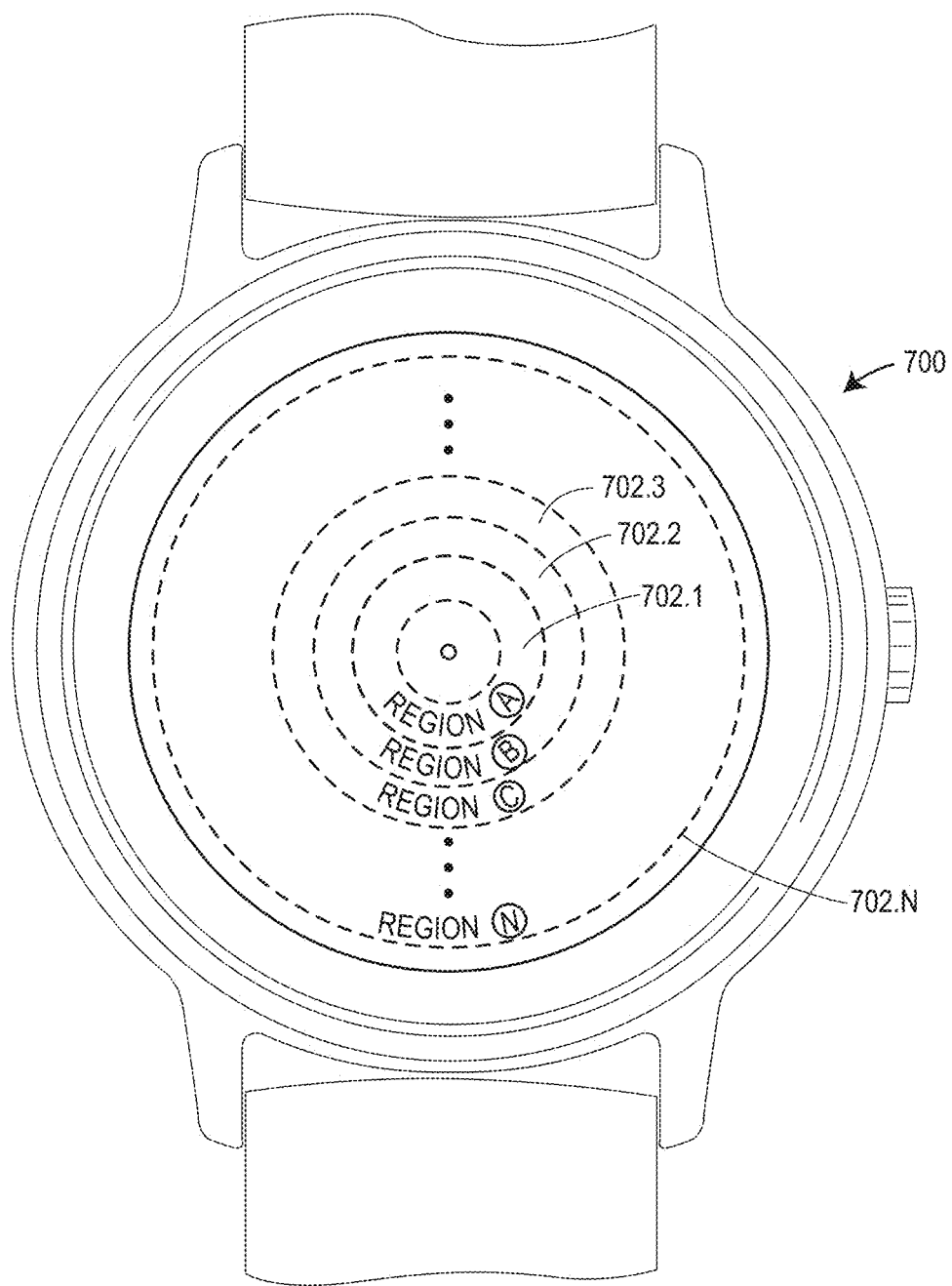
FIG. 7 is an illustration of an exemplary multidisc arrangement 700, according to an embodiment.

FIG. 7 is an illustration of an exemplary multidisc arrangement 700, according to an embodiment. In an embodiment, multidisc arrangement 700 may replace multicolored discs 302 and 304, as shown in FIG. 3, to provide analog wellness with alternative functionality. In this way, common components of analog wellness device 102 may be maintained among several different embodiments, while other components (e.g., watch face 206, fitness activity goal multicolored disc 208, an inactivity multicolored disc 210) may be substituted for other components.

In an embodiment, multidisc arrangement 700 may include any suitable number N of discs 702.1-702.N, each having an associated region A-N. Each of regions A-N may be grouped or positioned according to the type of information and/or the functionality represented within each respective region. Similar to fitness activity goal multicolored disc 208 and inactivity multicolored disc 210, as shown in FIG. 2, each of discs 702.1-702.N may be coupled to and rotated by one or more respective motors housed within the analog wellness device.

As will be further discussed below with specific examples, each of discs 702.1-702.N may include any suitable number and/or type of different colors, textures, labels, text, emoticons, symbols, emoji, indicia, graphics, etc., positioned at various regions A-N corresponding to the particular information that is to be conveyed to a user. Discs 702.1-702.N may each have a corresponding size and/or shape such that the width taken up by each of regions A-N are the same or different than one another. For example, the radial distance of each of regions A-C may occupy the same radial width as one another, while the radial distance from the outside of disc 702.3 to 702.N may be larger, such that region N may include additional space to provide information than regions 702.1-702.3.

To take advantage of the varying region sizes, a corresponding watch face may include any suitable number of windows, which may be of any suitable shape, orientation, and/or size, and positioned on the watch face such that various information is shown through the windows as each of discs 702.1-702.N rotates. In an embodiment, one or more of discs 702.1-702.N may be stacked on top of one another, with discs 702 lower in the stack and having a larger diameter than those on the top of the stack. In this way, multiple discs 702 may be stacked together to save space, and rotated to provide different information at different radial locations through a matching watch face.

Figure 8:
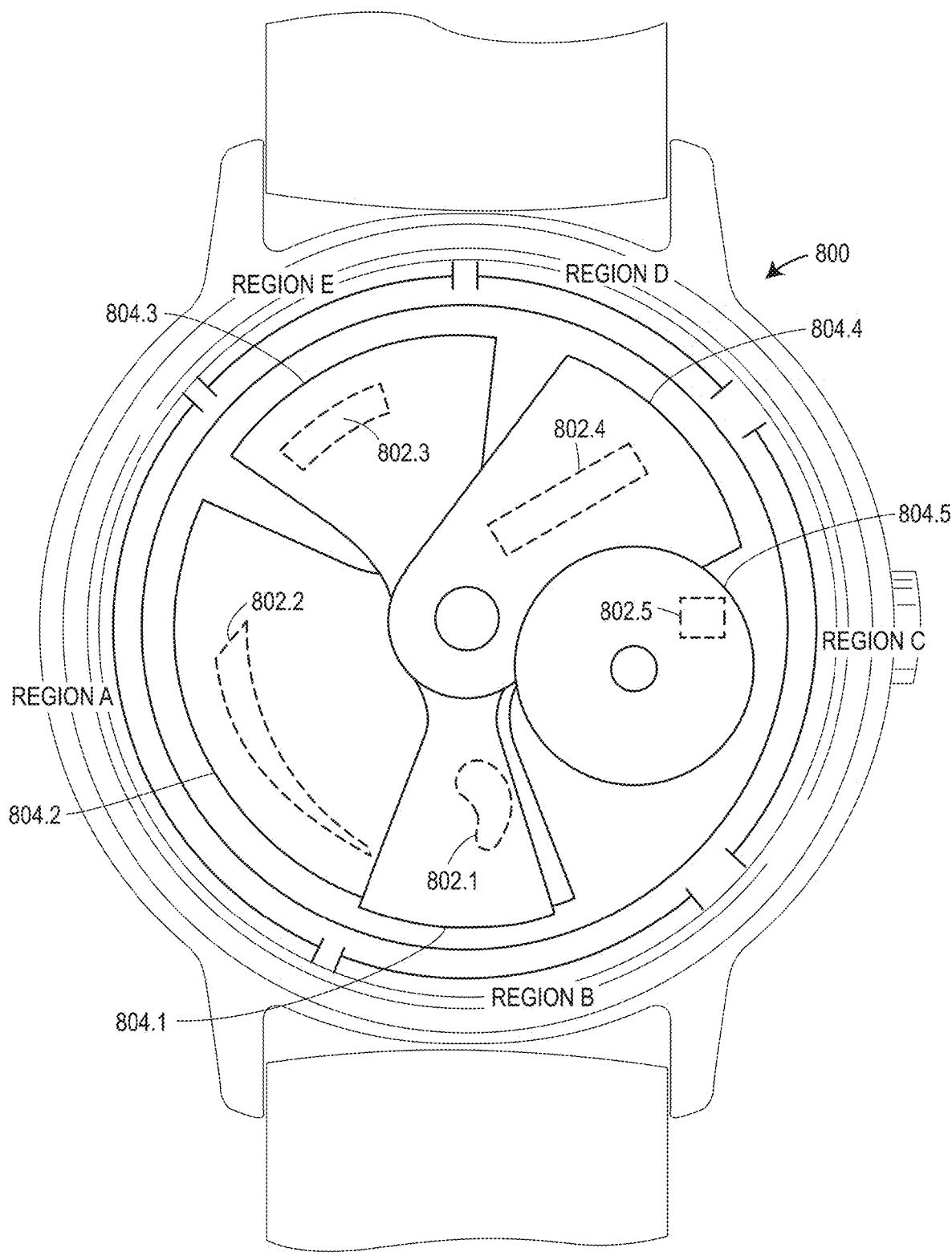
FIG. 8 is an illustration of an exemplary partial multidisc arrangement 800, according to an embodiment.

FIG. 8 is an illustration of an exemplary partial multidisc arrangement 800, according to an embodiment. Partial multidisc arrangement 800 may include any suitable number of partials discs having any suitable size and/or shape. For example, as shown in FIG. 8, partial multidisc arrangement 800 includes five partial discs 804.1-804.5 having a wedge shape and an associated region A-E. Similar to discs 702.1-702.N, as shown in FIG. 7, each of partial discs 804.1-804.5 may include any suitable number and/or type of different colors, textures, labels, text, emoticons, emoji, symbols, indicia, graphics, etc., positioned at various regions A-E corresponding to the particular information that is to be conveyed to a user.

As shown in FIG. 8, partial multidisc arrangement 800 illustrates windows 802.1-802.5, which allow the various information associated with each of partial discs 804.1-804.5 to be indicated to a user through a corresponding window as each partial disc 804 rotates. In various embodiments, windows 802.1-802.5 may be of any suitable size, shape, and/or orientation, such as radial (e.g., window 802.4) or annual (e.g., windows 802.2 and 802.3). By varying the size of windows 802 in such a manner, greater flexibility may be attained with regards to how information is indicated within each of regions A-E, as well as the size and shape of partial discs 804.

In some embodiments, the movement of one or more of partial discs 804 may be limited such that, as each partial disc 804 sweeps through its corresponding region, the partial discs 804 do not overlap with one another.

But in other embodiments, the movement of one or more of partial discs 804 may be implemented such that one or more of partial discs 804 shares one or more regions with other adjacent partial discs 804. In accordance with such embodiments, partial discs 804 may be on separate planes than one another or otherwise be shaped to facilitate a single partial disc 804 rotating and indicating information in more than one of regions A-E.

Figure 9:
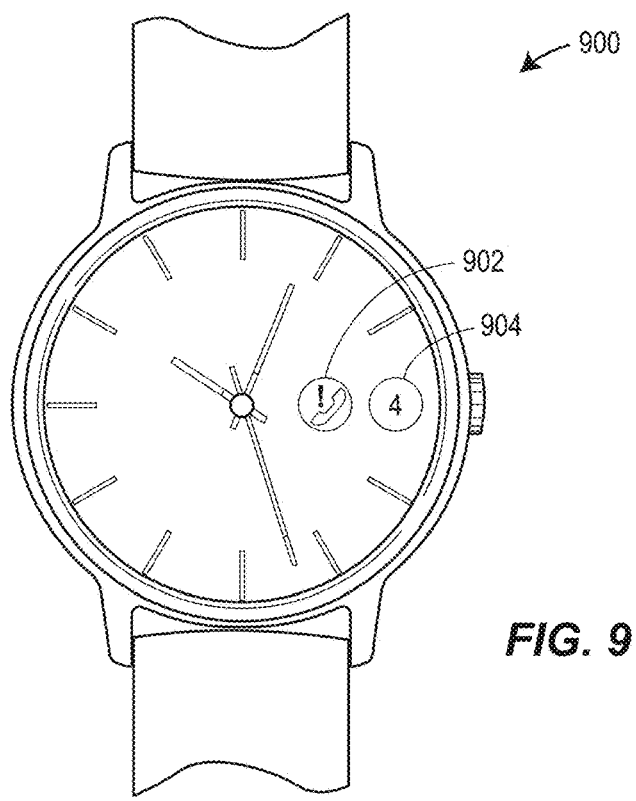
FIG. 9 is an illustration of an exemplary analog watch 900 indicating notifications associated with a mobile phone, according to an embodiment.

FIG. 9 is an illustration of an exemplary analog watch 900 providing notifications associated with a mobile phone, according to an embodiment. In an embodiment, analog watch 900 may be an implementation of analog wellness device 102, for example, as shown in FIG. 1. When connected to a mobile computing device (e.g., a mobile phone) embodiments include analog watch 900 indicating information associated with the mobile phone, as previously discussed with respect to FIG. 2. For example, analog watch 900 includes two windows 902 and 904. Window 902 indicates an icon indicating that the mobile phone has at least one missed call, while window 904 indicates an icon indicating that there have been 4 missed calls. Again, this information may be received, for example, via communications between analog watch 900 and the mobile phone (e.g., BLUETOOTH communications).

Figure 10:
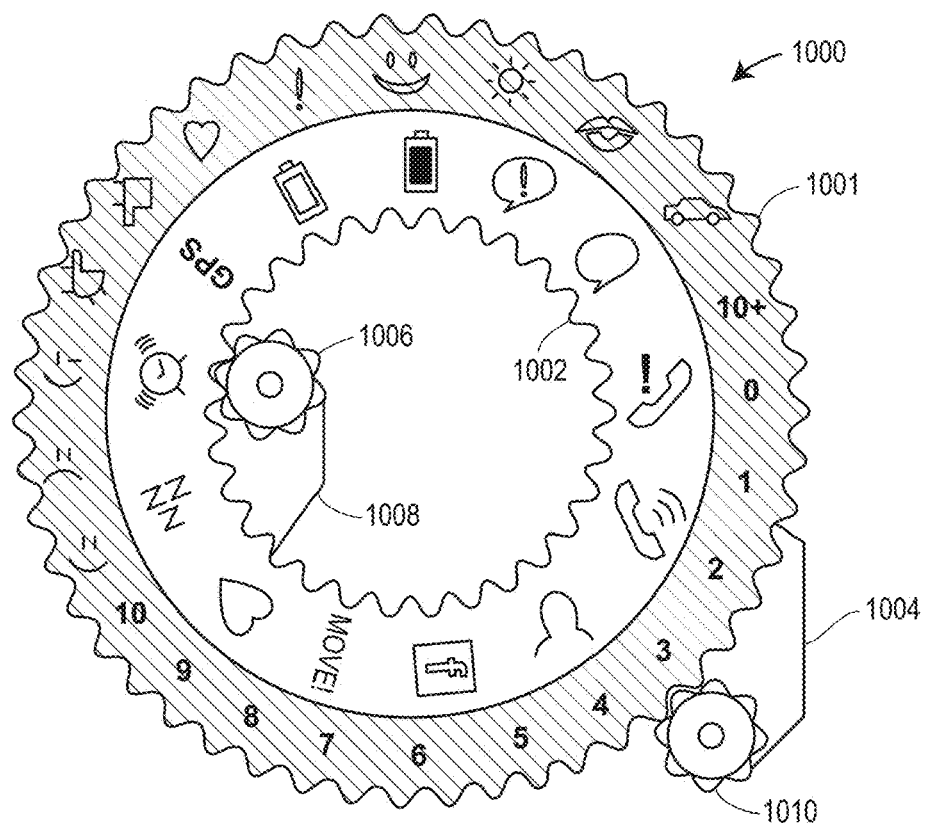
FIG. 10 is an illustration of an exemplary multidisc arrangement 1000 corresponding to the exemplary analog watch 900, according to an embodiment.

FIG. 10 is an illustration of an exemplary multidisc arrangement 1000 corresponding to the exemplary analog watch 900, as shown in FIG. 9, according to an embodiment. Multidisc arrangement 1000 may include a first disc 1001, which is rotated as gear 1010 rotates via motor 1004. Multidisc arrangement 1000 may also include a second disc 1002, which is rotated as gear 1006 rotates via motor 1008. As seen FIG. 10, the information presented on the top surface of the first disc 1001 and second disc 1002 may include a battery status, an alarm, fitness reminder (e.g., a "Move!" indication), missed messages, new messages, missed call, incoming call, social media indications, indication of favorites, images of a person, numbers, emoticons and any other graphical symbol.

Embodiments include gears 1010 and 1006 being coupled to their respective discs 1001 and 1002, respectively, in any suitable manner and/or configuration to facilitate the rotation of discs 1001 and 1002. In embodiment, motors 1004 and 1008 may correspond to motors 212 and 214, for example, as shown in FIG. 2.

Referring back to FIG. 9, analog watch 900 indicates information via windows 902 and 904. Multidisc arrangement 1000 may be an implementation of the underlying disc movement that results in this information being indicated. For example, as first disc 1001 rotates, the number "4" may be shown in window 904. Similarly, as second disc 1002 rotates, the icon associated with the missed call may be shown through window 902.

Figure 13:
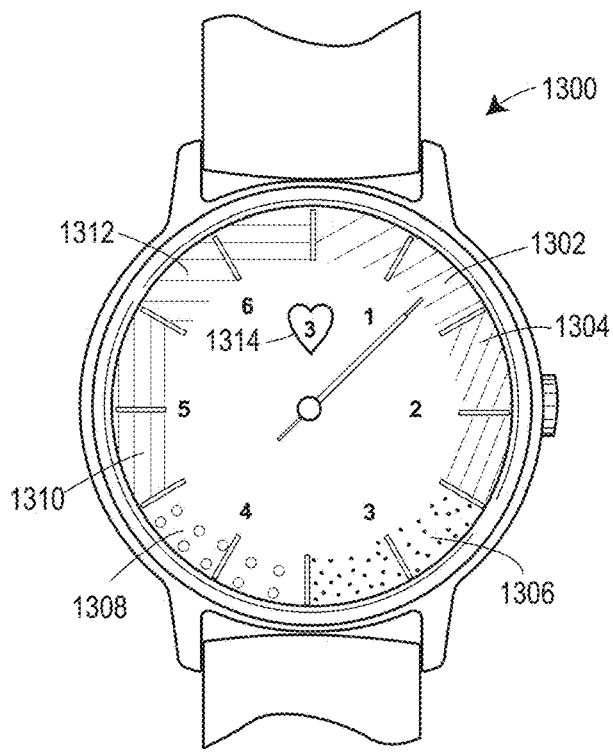
FIG. 13 is an illustration of an exemplary analog watch 1300 indicating heart rate information, according to an embodiment.

As described below, FIGS. 11-13 are illustrations of an exemplary analog watch indicating information associated with various embodiments. In each of FIGS. 11-13, the illustrated analog watch may be an implementation of analog wellness device 102, as shown in FIG. 1. FIGS. 11-13 show several examples of information that may be indicated on an analog watch in accordance with various embodiments. These examples are not intended to be limiting, as analog wellness device 102 may be configured to indicate any suitable type of information in accordance with the embodiments as described herein, and may indicate a combination of information from two or more embodiments. For example, analog wellness device 102 may indicate, in addition to the information discussed with regards to FIGS. 11-13, activity and/or inactivity data.

FIGS. 11A-11D show an exemplary analog watch indicating notifications associated with a mobile phone when the analog wellness device is connected to such a device.

Figure 11A:
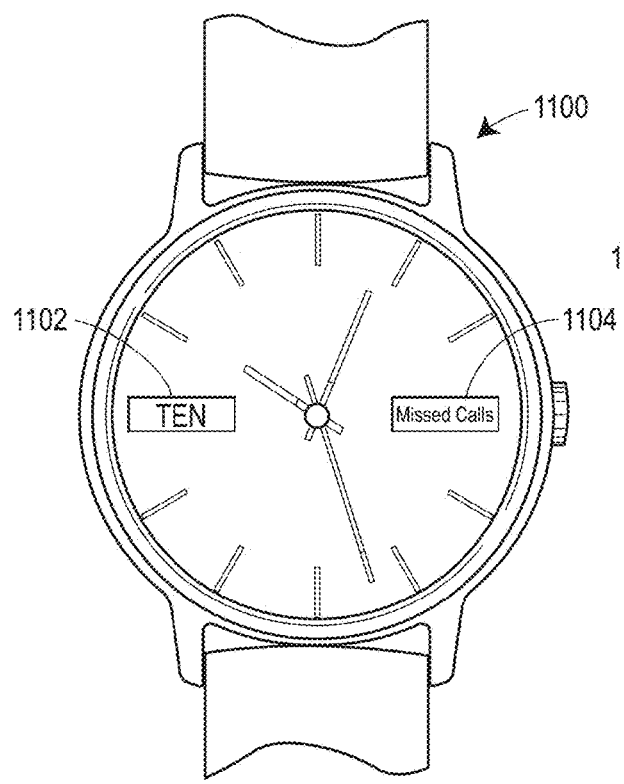
FIG. 11A is an illustration of an exemplary analog watch 1100 indicating missed call notifications associated with a mobile phone, according to an embodiment.

FIG. 11A is an illustration of an exemplary analog watch 1100 indicating missed call notifications associated with a mobile phone, according to an embodiment. As shown in FIG. 11A, analog watch 1100 includes two windows 1102 and 1104. Window 1102 shows an indication regarding a number of missed calls, while window 1104 shows an indication that the mobile phone connected to analog watch 1100 has missed at least one call.

Figure 11B:
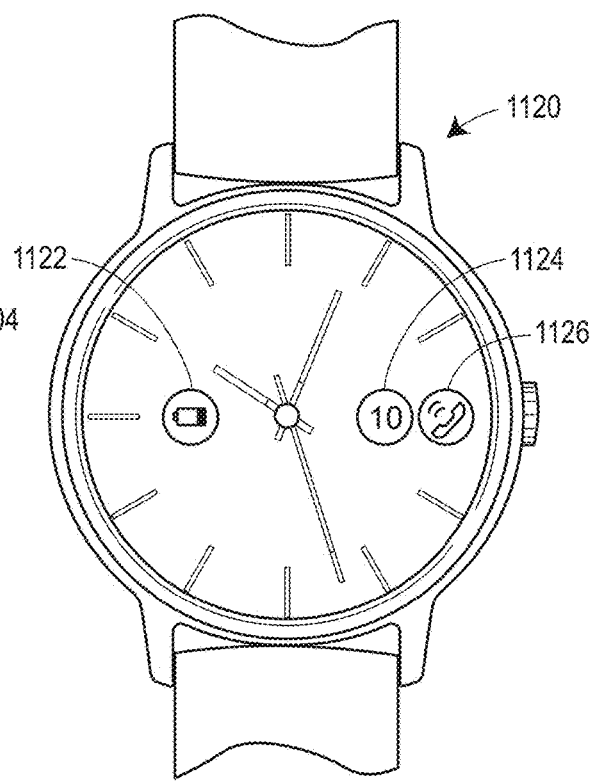
FIG. 11B is an illustration of an exemplary analog watch 1120 indicating missed call notifications and battery level information associated with a mobile phone, according to an embodiment.

FIG. 11B is an illustration of an exemplary analog watch 1120 indicating missed call notifications and battery level information associated with a mobile phone, according to an embodiment. As shown in FIG. 11B, analog watch 1120 includes three windows 1122, 1124, and 1126. Window 1122 shows a notification that the mobile phone connected to analog watch 1120 has a low battery, window 1124 shows an indication regarding a number of missed calls, while window 1126 shows an indication that the mobile phone connected to analog watch 1120 is receiving an incoming call.

Figure 11C:
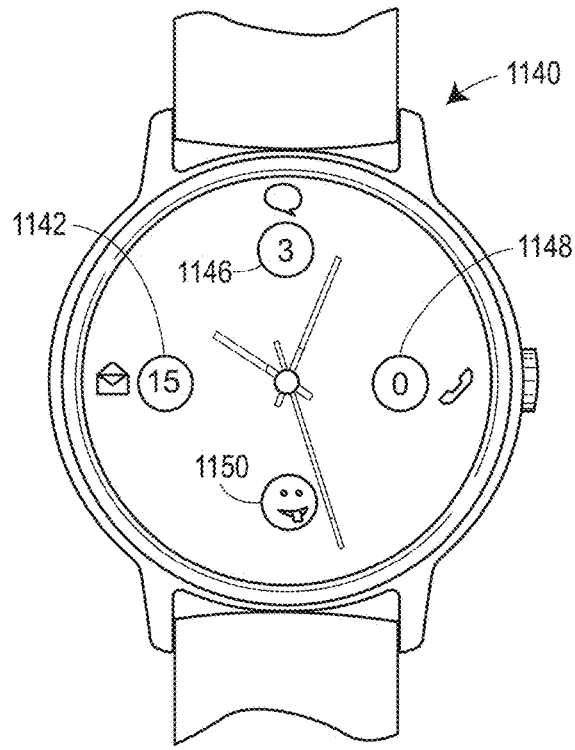
FIG. 11C is an illustration of an exemplary analog watch 1140 indicating various communication information associated with a mobile phone, according to an embodiment.

FIG. 11C is an illustration of an exemplary analog watch 1140 indicating various communication information associated with a mobile phone, according to an embodiment. As shown in FIG. 11C, analog watch 1140 includes four windows 1142, 1146, 1148, and 1150. In the example shown in FIG. 11C, windows 1142, 1146, and 1148 are associated with dedicated mobile phone functions. For example, window 1142 indicates a number of new and/or unread email messages, as indicated by the icon to the left of window 1142. Furthermore, window 1146 indicates a number of unread and/or new text messages, as indicated by the icon on top of window 1146. Additionally, window 1148 shows an indication regarding a number of missed calls, as indicated by the icon to the right of window 1148.

In some embodiments analog watch 1140 may include one or more windows that may or may not be associated with dedicated mobile phone functions. For example, as shown in FIG. 11C, window 1150 shows an emoji. In an embodiment, the emoji may be sent to the mobile phone as part of a text message, as a separate messaging application, etc. Analog watch 1140 may change the emoji indicated in window 1150 to provide any suitable number and types of emoji, for example, as additional ones are received at the mobile phone.

Figure 11D:
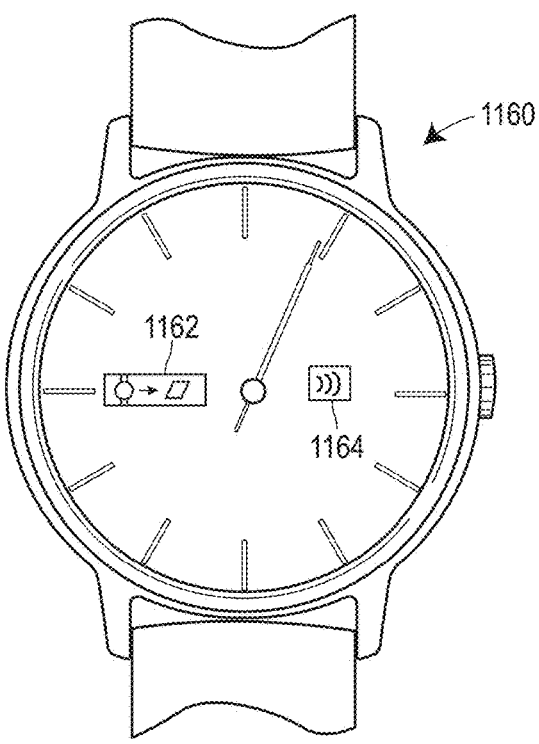
FIG. 11D is an illustration of an exemplary analog watch 1160 indicating connection status information, according to an embodiment.

FIG. 11D is an illustration of an exemplary analog watch 1160 indicating connection status information, according to an embodiment. As shown in FIG. 11D, analog watch 1160 includes two windows 1162 and 1164. Window 1162 shows a connection status indicating that the mobile phone is connected to analog watch 1160, while window 1164 shows a Wi-Fi connection indication, which may indicate an open Wi-Fi network has been detected, that analog watch 1160 is connected to a Wi-Fi network, etc.

FIGS. 12A-12C show an exemplary analog watch indicating information related to a user playing golf. For example, a user may use one or more off-the-shelf products that contain information such as golf course maps, topographic layouts, latitude-longitude coordinates of one or more holes, calculations regarding the par for each hole, calculations regarding lay-up yardage and/or club information, etc. Additionally or alternatively, analog wellness device 102 may support one or more functions that would otherwise be performed by the off-the-shelf product. In an embodiment, a user may interact with an off-the-shelf product to connect the product to analog wellness device 102 to download data to analog wellness device 102.

In various embodiments, the functions discussed below may be performed based upon a current golf course hole that is being played, which may be determined using any suitable techniques. For example, the current golf course hole may be determined based upon the user's direction and position while teeing off, which may be ascertained from one or more magnetometers (e.g., those included in sensor array 108). To provide another example, the analog watch may track its location while the user is traversing a golf course (e.g., via location determining component 109) to update the golfer's location on a downloaded golf course map while playing the course to determine each next hole.

FIG. 12A is an illustration of an exemplary analog watch 1200 indicating golf course navigational information, according to an embodiment. As shown in FIG. 12A, analog watch 1200 includes four windows 1204, 1206, 1208, and 1210. Similar to analog watch 1140, in the example shown in FIG. 12A, windows 1204, 1206, 1208, and 1210 are associated with dedicated functions but related to indicating golfing information while a user is playing a golf course.

Window 1204 shows a distance between analog watch 1200 and a golf course location, which may be associated with the hole or other location entered by a user via another external computing device. For example, analog watch 1200 may determine its location (e.g., via location determining component 109) and compare this to a golf course hole location. Using the difference between these coordinates, analog watch 1200 may indicate the distance to the hole in window 1204.

In an embodiment, analog hands 1202 may perform functions in addition to indicating the time on analog watch 1200. Continuing the previous example, analog hands 1202 may point in a direction to the golf course hole location, such that analog watch 1200 indicates both a distance and direction to the golf course hole location, which may dynamically update over time as the user moves towards the golf course hole location.

Again, analog watch 1200 may calculate, based upon any suitable combination of local processing and/or downloaded data, yardage to the front, center, and back of the green for a current hole that is being played. Embodiments include windows 1206, 1208, and 1210 indicating front, center, and back yardage information, respectively, for an approaching green based upon the location of analog watch 1200 relative to the current hole.

FIG. 12B is an illustration of an exemplary analog watch 1220 indicating golf scoring information, according to an embodiment. As shown in FIG. 12B, analog watch 1220 includes two windows 1222 and 1224. Similar to analog watch 1200, in the example shown in FIG. 12A, windows 1222 and 1224 are associated with dedicated functions related to indicating golfing information while a user is playing a golf course.

Window 1222 indicates a stroke count for a particular hole a golfer is playing, while window 1224 indicates par information for the same hole. The stroke count may be determined, for example, based upon an analysis of motion data (e.g., via sensor array 108) that matches a golf swing motion profile.

FIG. 12C is an illustration of an exemplary analog watch 1240 indicating golf strategy information, according to an embodiment. As shown in FIG. 12C, analog watch 1240 includes six windows 1242, 1244, 1246, 1248, 1250, and 1252. Similar to analog watch 1200, in the example shown in FIG. 12A, windows 1242, 1244, 1246, 1248, 1250, and 1252 are associated with dedicated functions related to indicating golfing information while a user is playing a golf course.

Although the six windows are shown as being separate in FIG. 12C, embodiments include the information being indicated in each of the six windows on analog watch 1240 in a way that correlates this information. For example, based upon a location of analog watch 1240 on a golf course, analog watch 1240 may calculate (e.g., via execution of instructions stored in notifications module 128 via processor 106) three options for lay-ups from the user's location on the golf-course and their associated clubs.

In an embodiment, each club may be identified with its corresponding lay-up yardage information by a common radial distance from the center of analog watch 1240. For example, window 1246 indicates a driver club, while window 1248 indicates a matching lay-up yardage calculation of 195 yards for a user playing this club. Similarly, window 1244 indicates a 9-iron club, while window 1250 indicates a matching lay-up yardage calculation of 135 yards for a user playing the 9-iron. To provide another example, window 1242 indicates a wedge, while window 1252 indicates a matching lay-up yardage calculation of 110 yards for a user playing the wedge.

FIG. 13 is an illustration of an exemplary analog watch 1300 indicating heart rate information, according to an embodiment. In an embodiment, analog watch 1300 may include any suitable number of heart rate zones. For example, as shown in FIG. 13, analog watch 1300 indicates six heart rate zones 1302, 1304, 1306, 1308, 1310, and 1312. These heart rate zones may be associated with, for example, any suitable range of a target heart rate, such as 80% to 130%, 90% to 140%, etc. In some embodiments, a user may download an association of target zone percentages with the indicated target zones from a connected external computing device. In other embodiments, the target zone percentages may be predetermined and/or preprogrammed into the memory (e.g., memory 118) of analog watch 1300.

As previously discussed with reference to analog watch 1200, as shown in FIG. 12A, the hands of analog watch 1300 may likewise have a dual-purpose: telling time and pointing to the target hear rate zones. In an embodiment, a user's heart rate may be detected (e.g., via sensor array 108), compared to the user-specified (downloaded) and/or predetermined target zones, and the hands of analog watch 1300 may point to one of heart rate zones 1302, 1304, 1306, 1308, 1310, and 1312 based upon the user's heart rate. Embodiments include analog watch 1300 dynamically updating the hand locations as the user's heart rate changes. Additionally or alternatively, analog watch 1300 may indicate the user's current heart rate target zone in a window, such as window 1314, for example.

Although the foregoing text sets forth a detailed description of numerous different embodiments, it should be understood that the detailed description is to be construed as exemplary only and does not describe every possible embodiment because describing every possible embodiment would be impractical, if not impossible. In light of the foregoing text, numerous alternative embodiments may be implemented, using either current technology or technology developed after the filing date of this patent application.

What is claimed is:

1. A watch, comprising:
    a watch face configured to indicate time in analog form, the watch face including a first window;
    a biometrics sensor configured to output biometric signals associated with a user wearing the watch;
    a first motor;
    a first disc coupled with the first motor and including a plurality of alphanumeric characters, the plurality of alphanumeric characters including a plurality of target heart rate zones and the first disc positioned under the first window such that one of the plurality of alphanumeric characters is visible through the first window as the first motor rotates the first disc; and
    a processor coupled with the biometrics sensor and the first motor, the processor configured to:
    determine biometric information for the user based on the biometric signals, the determined biometric information including the user's heart rate,
    determine a target heart rate zone for the user of the watch,
    select one of the plurality of target heart rate zones based upon the determined heart rate for the user, and
    command the first motor to rotate the first disc to position the selected target heart rate zone as being visible through the first window.

2. The watch of claim 1, further comprising:
    a second motor; and
    a second disc coupled with the second motor and including a plurality of notification icons, the plurality of notification icons including a notification icon corresponding to a selected alphanumeric character;
    wherein the second disc is positioned under a second window such that one of the plurality of notification icons is visible through the second window as the second motor rotates the second disc; and
    wherein the watch face further includes the second window.

3. The watch of claim 2, wherein the first window is proximate to the second window within the watch face.

4. The watch of claim 2, wherein the notification icon is a fitness reminder.

5. The watch of claim 2, wherein the notification icon is a missed calls symbol.

6. The watch of claim 2, wherein the notification icon is a battery level symbol.

7. The watch of claim 1, wherein the biometrics sensor is configured to determine the heart rate for the user wearing the watch.

8. The watch of claim 7, further comprising watch hands coupled with the processor, wherein the watch face includes a plurality of heart rate zones, and wherein the processor is configured to control the watch hands to rotate to a location of the watch hands associated with one of the plurality of heart rate zones corresponding to the determined heart rate.

9. A watch, comprising:
- a watch face configured to indicate time in analog form, the watch face including a first window and a second window;
- a biometrics sensor configured to output biometric signals associated with a user wearing the watch;
- a communication unit configured to wirelessly receive communications from an external computing device;
- a first motor;
- a second motor;
- a first disc coupled with the first motor and including a plurality of alphanumeric characters, the plurality of alphanumeric characters including a plurality of target heart rate zones and the first disc positioned under the first window such that one of the plurality of alphanumeric characters is visible through the first window as the first motor rotates the first disc;
- a second disc coupled with the second motor and including a plurality of notification icons, the second disc positioned under the second window such that one of the plurality of notification icons is visible through the second window as the second motor rotates the second disc; and
- a processor coupled with the biometrics sensor, the communication unit, the first motor, and the second motor, the processor configured to:
  - determine biometric information for the user based on the biometric signals,
  - determine a target heart rate zone for the user of the watch,
  - select one of the plurality of notification icons based on the received communications,
  - select one of the plurality of target heart rate zones based upon the determined biometric information,
  - command the first motor to rotate the first disc to position the selected target heart rate zone as being visible through the first window, and
  - command the second motor to rotate the second disc to position the selected notification icon as being visible through the second window.

10. The watch of claim 9, wherein the first window is proximate to the second window within the watch face.

11. The watch of claim 9, wherein the biometrics sensor is configured to determine a heart rate for the user wearing the watch.

12. The watch of claim 11, further comprising watch hands coupled with the processor, wherein the watch face includes a plurality of heart rate zones, and wherein the processor is configured to control the watch hands to rotate to a location of the watch hands associated with one of the plurality of heart rate zones corresponding to the determined heart rate.

13. The watch of claim 9, wherein the determined biometric information is the user's heart rate.

14. The watch of claim 9, wherein one of the plurality of notification icons is a fitness reminder.

15. A watch, comprising:
- a watch face configured to indicate time in analog form, the watch face including a first window and a second window;
- a biometric sensor configured to output biometric signals associated with a user wearing the watch;
- a first motor;
- a second motor;
- a first disc coupled with the first motor and including a plurality of alphanumeric characters, the plurality of alphanumeric characters including a plurality of target heart rate zones and the first disc positioned under the first window such that one of the plurality of alphanumeric characters is visible through the first window as the first motor rotates the first disc;
- a second disc coupled with the second motor and including a plurality of notification icons, the second disc positioned under the second window such that one of the plurality of notification icons is visible through the second window as the second motor rotates the second disc; and
- a processor coupled with the biometric sensor, the first motor, and the second motor, the processor configured to:
  - determine biometric information for the user based on the biometric signals,
  - determine a target heart rate zone for the user of the watch,
  - select one of the plurality of notification icons, the notification icons including an activity symbol associated with biometric information,
  - select one of the plurality of target heart rate zones based upon the determined biometric information,
  - command the first motor to rotate the first disc to position the selected target heart rate zone as being visible through the first window, and
  - command the second motor to rotate the second disc to position the activity symbol as being visible through the second window.

16. The watch of claim 15, wherein the determined biometric information is the user's heart rate.

17. The watch of claim 15, further comprising watch hands coupled with the processor, wherein the watch face includes a plurality of heart rate zones, and wherein the processor is configured to control the watch hands to rotate to a location of the watch hands associated with one of the plurality of heart rate zones corresponding to the determined heart rate.

* * * * *